US012778755B2

(12) United States Patent
Kalpakci et al.

(10) Patent No.: US 12,778,755 B2
(45) Date of Patent: Nov. 3, 2026

(54) BONE IMPLANT FOR ENCLOSING BONE MATERIAL

(71) Applicant: WARSAW ORTHOPEDIC INC., Warsaw, IN (US)

(72) Inventors: Kerem N. Kalpakci, Memphis, TN (US); Jared J. Diegmueller, Memphis, TN (US); Jason A. Rister, Memphis, TN (US); Daniel A. Shimko, Germantown, TN (US); Scott M. Vickers, Hernando, MS (US); Jeffrey L. Scifert, Arlington, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 744 days.

(21) Appl. No.: 18/322,915

(22) Filed: May 24, 2023

(65) Prior Publication Data

US 2023/0293305 A1 Sep. 21, 2023

Related U.S. Application Data

(62) Division of application No. 15/656,112, filed on Jul. 21, 2017, now Pat. No. 11,666,446.

(51) Int. Cl.
*A61F 2/28* (2006.01)
*A61F 2/30* (2006.01)

(52) U.S. Cl.
CPC ........ *A61F 2/2846* (2013.01); *A61F 2/30907* (2013.01); *A61F 2002/2835* (2013.01); (Continued)

(58) Field of Classification Search
CPC ..................... A61F 2/2846; A61F 2002/30062
See application file for complete search history.

(56) References Cited

U.S. PATENT DOCUMENTS 5,549,388 A 8/1996 Wilkes
7,226,481 B2 6/2007 Kuslich
(Continued)

FOREIGN PATENT DOCUMENTS

CN 1819806 A 8/2006
JP 2006-526486 A 11/2006
(Continued)

OTHER PUBLICATIONS

Office Action issued on Jan. 27, 2022 by the Japan Patent Office in corresponding Japanese application No. 2018-116766. English translation provided.
(Continued)

*Primary Examiner* — Brian A Dukert
(74) *Attorney, Agent, or Firm* — Sorell, Lenna & Schmidt, LLP

(57) ABSTRACT

A bone implant for enclosing bone material is provided. The bone implant comprises a mesh having an inner surface and an outer surface opposing the inner surface. The inner surface is configured to receive a bone material when the inner surface of the mesh is in an open configuration. A plurality of projections are disposed on or in at least a portion of the inner surface of the mesh. The plurality of projections extend from at least the portion of the inner surface of the mesh and are configured to engage a section of the inner surface of the mesh or a section of the outer surface of the mesh or both sections of the inner and outer surfaces of the mesh in a closed configuration so as to enclose the bone material. A tray, a kit and a method of making the bone implant are also provided.

11 Claims, 7 Drawing Sheets

(52) U.S. Cl.
CPC ............... *A61F 2002/30062* (2013.01); *A61F 2002/30383* (2013.01); *A61F 2002/30467* (2013.01); *A61F 2002/30914* (2013.01); *A61F 2310/00293* (2013.01); *A61F 2310/00359* (2013.01); *A61F 2310/00371* (2013.01)

(56) References Cited

U.S. PATENT DOCUMENTS

| | | | |
|---|---|---|---|
| 7,252,685 B2 * | 8/2007 | Bindseil ................ A61F 2/4455 606/76 |
| 7,341,601 B2 | 3/2008 | Eisermann et al. |
| 8,540,752 B2 | 9/2013 | de Moura |
| 9,039,783 B2 | 5/2015 | Petter-Puchner et al. |
| 9,095,569 B2 | 8/2015 | Shoseyov et al. |
| 9,101,475 B2 | 8/2015 | Wei et al. |
| 9,179,994 B2 | 11/2015 | Stopek et al. |
| 9,198,758 B2 | 12/2015 | McKay |
| 9,220,598 B2 | 12/2015 | Betz et al. |
| 9,241,797 B2 | 1/2016 | McKay |
| 9,333,082 B2 | 5/2016 | Wei .................... A61B 17/7097 |
| 9,492,278 B2 | 11/2016 | Wei et al. |
| 2004/0249471 A1 | 12/2004 | Bindseil et al. |
| 2009/0157087 A1 | 6/2009 | Wei et al. |
| 2011/0054408 A1 | 3/2011 | Wel et al. |
| 2011/0144764 A1 * | 6/2011 | Bagga ..................... A61P 19/00 424/602 |
| 2012/0253109 A1 | 10/2012 | VanDeWeghe et al. |
| 2013/0296897 A1 | 11/2013 | Trupiano et al. |
| 2014/0031795 A1 | 1/2014 | McKay |
| 2014/0212471 A1 | 7/2014 | Drapeau et al. |
| 2015/0306278 A1 | 10/2015 | McKay |
| 2016/0038207 A1 | 2/2016 | Wei et al. |
| 2016/0250038 A1 | 9/2016 | Wei et al. |
| 2016/0318247 A1 | 11/2016 | Schlachter |

FOREIGN PATENT DOCUMENTS

| | | |
|---|---|---|
| WO | 2004/108023 | 12/2004 |
| WO | 2004/108023 A1 | 12/2004 |
| WO | 2012/068062 A1 | 5/2012 |
| WO | 2015/157554 A1 | 10/2015 |
| WO | 2016/160180 A1 | 10/2016 |
| WO | 2016/160183 A1 | 10/2016 |

OTHER PUBLICATIONS

Chinese Office Action issued by the China State IP Office dated Sep. 3, 2021 in corresponding Chinese patent application No. 20180775452.5. English translation provided.

Extended European Search Report dated Oct. 9, 2020 issued by the European Patent Office in corresponding European patent application No. 20179242.1 in the name of Warsaw Orthopedic, Inc.

Extended European Search Report, mailed Dec. 21, 2018, issued by the European Patent Office in EP Application No. 18178778.9 for Bone Implant for Enclosing Bone Material filed on Jun. 20, 2018.

* cited by examiner

BONE IMPLANT FOR ENCLOSING BONE MATERIAL

BACKGROUND

The use of bone grafts and bone substitute materials in orthopedic medicine is known. While bone wounds can regenerate without the formation of scar tissue, fractures and other orthopedic injuries take a long time to heal, during which time the bone is unable to support physiologic loading unaided. Metal pins, screws, rods, plates and meshes are frequently required to replace the mechanical functions of injured bone. However, metal is significantly more stiff than bone. Use of metal implants may result in decreased bone density around the implant site due to stress shielding. Physiologic stresses and corrosion may cause metal implants to fracture. Unlike bone, which can heal small damage cracks through remodeling to prevent more extensive damage and failure, damaged metal implants can only be replaced or removed. The natural cellular healing and remodeling mechanisms of the body coordinate removal of bone and bone grafts by osteoclast cells and formation of bone by osteoblast cells.

Conventionally, bone tissue regeneration is achieved by filling a bone repair site with a bone graft. Over time, the bone graft is incorporated by the host and new bone remodels the bone graft. In order to place the bone graft, it is common to use a monolithic bone pre-formed graft or to form an osteoimplant comprising particulated bone in a carrier. Generally, the formed implant, whether monolithic or particulated and in a carrier is substantially solid at the time of implantation and thus does not conform to the implant site. The implant is also substantially complete at the time of implantation and thus provides little ability for customization, for example by the addition of autograft or alteration of the shape of the implant.

The use of bone grafts is generally limited by the available shape and size of grafts. Further, bone grafts using cortical bone remodel slowly because of their limited porosity. Traditional bone substitute materials are more quickly remodeled but cannot immediately provide mechanical support. In addition, while bone substitute materials can be used to fill oddly shaped bone defects by themselves, such materials are not as well suited for wrapping or resurfacing bone.

Therefore, it would be beneficial to provide bone implants that can be filled with bone material (e.g., natural bone particles and/or synthetic bone particles) and can be easily sealed and implanted at a surgical site. Bone implants that can be customized to the size and shape of the bone defect as well as to the type of bone material to be used would be desirable. Kits and methods relating to filling and implanting these bone implants would also be desirable.

SUMMARY

Bone implants are provided that can be filled with bone material and can be easily sealed and implanted at a surgical site. The bone implants can be customized to the size and shape of the bone defect as well as to the type of bone material to be used. Kits and methods relating to filling and implanting these bone implants are also provided.

In one embodiment, a bone implant for enclosing bone material is provided. The bone implant comprises a mesh having an inner surface and an outer surface opposing the inner surface. The inner surface is configured to receive a bone material when the inner surface of the mesh is in an open configuration. A plurality of projections is disposed on or in at least a portion of the inner surface of the mesh. The plurality of projections extend from at least the portion of the inner surface of the mesh and are configured to engage a section of the inner surface of the mesh or a section of the outer surface of the mesh or both sections of the inner and outer surfaces of the mesh in a closed configuration so as to enclose the bone material.

In one embodiment, a kit for filling bone material in a bone implant is provided. The kit comprises a bone implant comprising a mesh having an inner surface and an outer surface opposing the inner surface. The inner surface is configured to receive a bone material when the inner surface of the mesh is in an open configuration. A plurality of projections is disposed on or in at least a portion of the inner surface of the mesh. The plurality of projections extend from at least the portion of the inner surface of the mesh and are configured to engage a section of the inner surface of the mesh or a section of the outer surface of the mesh or both sections of the inner and outer surfaces of the mesh in a closed configuration, so as to enclose the bone material. A tray is also provided having a proximal end, a distal end, and a longitudinal recess disposed therebetween. The longitudinal recess is configured to receive the mesh in the open configuration to allow filling of the bone material into the bone implant.

In one embodiment, a method of implanting a bone implant at a surgical site is provided. The method comprises providing a bone implant comprising a mesh having an inner surface and an outer surface opposing the inner surface, the inner surface configured to receive a bone material when the inner surface of the mesh is in an open configuration; a plurality of projections disposed on or in at least a portion of the inner surface of the mesh, the plurality of projections extending from at least the portion of the inner surface of the mesh and configured to engage a section of the inner surface of the mesh or a section of the outer surface of the mesh or both sections of the inner and outer surfaces of the mesh in a closed configuration so as to enclose the bone material; disposing the bone material in the inner surface of the mesh by orientating the mesh in the open configuration; enclosing the bone material in the mesh by orientating the mesh in the closed configuration; and placing the bone implant at the surgical site thereby implanting the bone implant at the surgical site.

While multiple embodiments are disclosed, still other embodiments of the present application will become apparent to those skilled in the art from the following detailed description, which is to be read in connection with the accompanying drawings. As will be apparent, the present disclosure is capable of modifications in various obvious aspects, all without departing from the spirit and scope of the present disclosure. Accordingly, the detailed description is to be regarded as illustrative in nature and not restrictive.

BRIEF DESCRIPTION OF THE FIGURES

The present disclosure will become more readily apparent from the specific description accompanied by the following drawings below.

Figure 1:
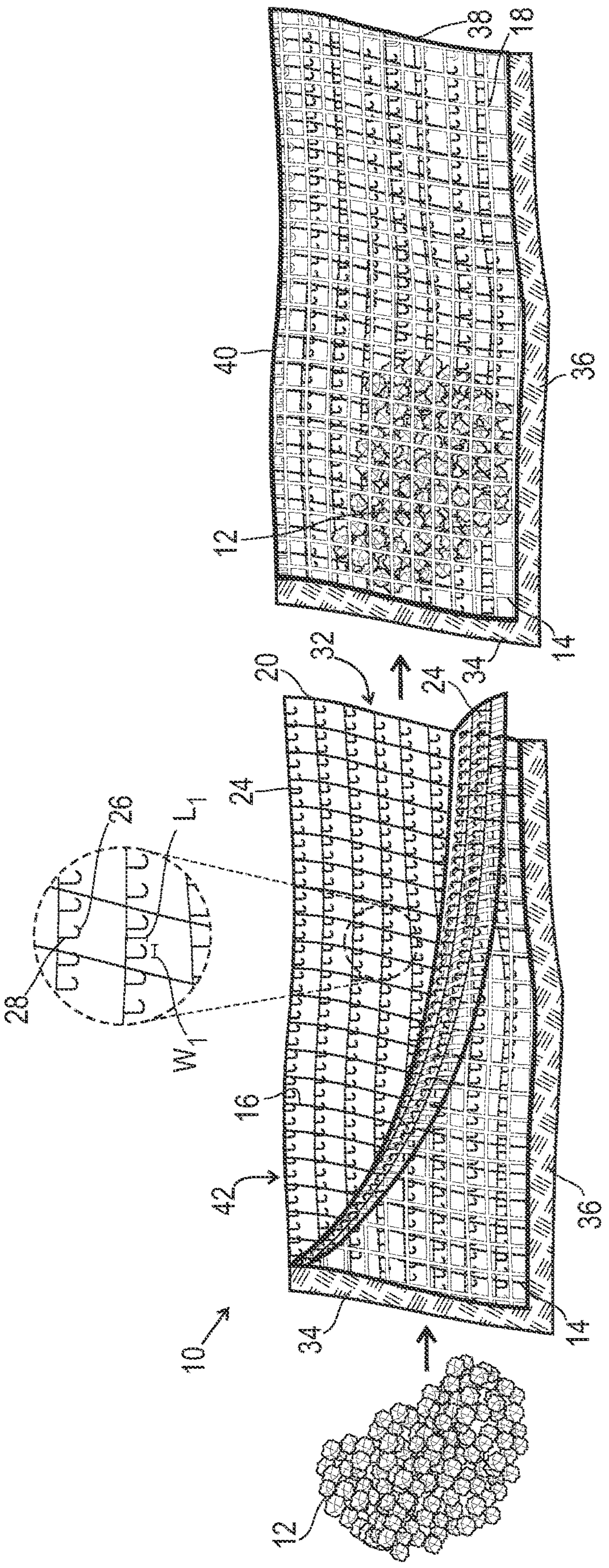
FIG. 1 illustrates a perspective view of a bone implant for enclosing bone material. The bone implant comprises a mesh having an inner surface and an outer surface opposing the inner surface. The inner surface is configured to receive a bone material when the inner surface of the mesh is in an open configuration. A plurality of projections are disposed on or in the inner surface of the mesh. The plurality of projections extend from the inner surface of the mesh and are configured to engage a section of the inner surface of the mesh or a section of the outer surface of the mesh or both sections of the inner and outer surfaces of the mesh in a closed configuration so as to enclose the bone material.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

Definitions

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Similarly, when values are expressed as approximations, by use of the antecedent "about," it will be understood that the particular value forms another embodiment that is +/−10% of the recited value. Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value.

Notwithstanding that the numerical ranges and parameters setting forth the broad scope of this application are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, for example, 5.5 to 10.

Bioactive agent or bioactive compound is used herein to refer to a compound or entity that alters, inhibits, activates, or otherwise affects biological or chemical events. For example, bioactive agents may include, but are not limited to, osteogenic or chondrogenic proteins or peptides, anti-AIDS substances, anti-cancer substances, antibiotics, immunosuppressants, anti-viral substances, enzyme inhibitors, hormones, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and antiadhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, anti-depressants, anti-psychotic substances, anti-emetics, and imaging agents. In certain embodiments, the bioactive agent is a drug. Bioactive agents further include RNAs, such as siRNA, and osteoclast stimulating factors. In some embodiments, the bioactive agent may be a factor that stops, removes, or reduces the activity of bone growth inhibitors. In some embodiments, the bioactive agent is a growth factor, cytokine, extracellular matrix molecule or a fragment or derivative thereof, for example, a cell attachment sequence such as RGD. In some embodiments, the bioactive active comprises nutraceuticals, including, but not limited to vitamin A, vitamin D, vitamin E, vitamin K2, isoflavones, milk proteins, caffeine, sugars or a combination thereof. A more complete listing of bioactive agents and specific drugs suitable for use in the present application may be found in Pharmaceutical Substances: Syntheses, Patents, Applications by Axel Kleemann and Jurgen Engel, Thieme Medical Publishing, 1999; Merck Index: An Encyclopedia of Chemicals, Drugs, and Biologicals, edited by Susan Budavari et al., CRC Press, 1996; and United States Pharmacopeia-25/National Formulary-20, published by the United States Pharmacopeia Convention, Inc., Rockville Md., 2001, each of which is incorporated herein by reference.

Biocompatible, as used herein, is intended to describe materials that, upon administration in vivo, do not induce undesirable long-term effects.

Bone, as used herein, refers to bone that is cortical, cancellous or cortico-cancellous of autogenous, allogenic, xenogenic, or transgenic origin.

Bone graft, as used herein, refers to any implant prepared in accordance with the embodiments described herein and therefore may include expressions such as bone material and bone membrane.

Demineralized, as used herein, refers to any material generated by removing mineral material from tissue, for example, bone tissue. In certain embodiments, demineralized bone material may be added to the bone void filler. The demineralized bone material described herein include preparations containing less than 5%, 4%, 3%, 2% or 1% calcium by weight. Partially demineralized bone (for example, preparations with greater than 5% calcium by weight but containing less than 100% of the original starting amount of calcium) is also considered within the scope of the disclosure. In some embodiments, partially demineralized bone contains preparations with greater than 5%, 10%, 15%, 20%, 25%, 30%, 35%, 40%, 45%, 50%, 55%, 60%, 65%, 70%, 75%, 80%, 85%, 90%, 95%, 96%, 97%, 98% or 99% of the original starting amount of calcium. In some embodiments, demineralized bone has less than 95% of its original mineral content. In some embodiments, demineralized bone has less than 95%, 90%, 85%, 80%, 75%, 70%, 65%, 60%, 55%, 50%, 45%, 40%, 35%, 30%, 25%, 20%, 15%, 10%, or 5% of its original mineral content. Demineralized is intended to encompass such expressions as "substantially demineralized," "partially demineralized," "superficially demineralized," and "fully demineralized." In some embodiments, part or all of the surface of the bone can be demineralized. For example, part or all of the surface of the bone material can be demineralized to a depth of from about 100 to about 5000 microns, or about 150 microns to about 1000 microns. In some embodiments, part or all of the surface of the bone material can be demineralized to a depth of from about 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350, 3400, 3450, 3500, 3550, 3600, 3650, 3700, 3750, 3800, 3850, 3900, 3950, 4000, 4050, 4100, 4150, 4200, 4250, 4300, 4350, 4400, 4450, 4500, 4550, 4600, 4650, 4700, 4750, 4800, 4850, 4900, 4950 to about 5000 microns. If desired, the bone material can comprise demineralized material.

Partially demineralized bone is intended to refer to preparations with greater than 5% calcium by weight but containing less than 100% of the original starting amount of calcium. In some embodiments, partially demineralized bone comprises 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and/or 99% of the original starting amount of calcium.

In some embodiments, the demineralized bone may be surface demineralized from about 1-99%. In some embodiments, the demineralized bone is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and/or 99% surface demineralized. In various embodiments, the demineralized bone may be surface demineralized from about 15-25%. In some embodiments, the demineralized bone is 15, 16, 17, 18, 19, 20, 21, 22, 23, 24 and/or 25% surface demineralized.

Demineralized bone matrix (DBM), as used herein, refers to any material generated by removing mineral material from bone tissue. In some embodiments, the DBM compositions as used herein include preparations containing less than 5% calcium and, in some embodiments, less than 1% calcium by weight. In some embodiments, the DBM compositions include preparations that contain less than 5, 4, 3, 2 and/or 1% calcium by weight. In other embodiments, the DBM compositions comprise partially demineralized bone (for example, preparations with greater than 5% calcium by weight but containing less than 100% of the original starting amount of calcium).

Osteoconductive, as used herein, refers to the ability of a substance to serve as a template or substance along which bone may grow.

Osteogenic, as used herein, refers to materials containing living cells capable of differentiation into bone tissue.

Osteoinductive, as used herein, refers to the quality of being able to recruit cells from the host that have the potential to stimulate new bone formation. Any material that can induce the formation of ectopic bone in the soft tissue of an animal is considered osteoinductive. For example, most osteoinductive materials induce bone formation in athymic rats when assayed according to the method of Edwards et al., "Osteoinduction of Human Demineralized Bone: Characterization in a Rat Model," Clinical Orthopaedics & Rel. Res., 357:219-228, December 1998, incorporated herein by reference.

Superficially demineralized, as used herein, refers to bone-derived elements possessing at least about 90 weight percent of their original inorganic mineral content. In some embodiments, superficially demineralized contains at least about 90, 91, 92, 93, 94, 95, 96, 97, 98 and/or 99 weight percent of their original inorganic material. The expression "fully demineralized" as used herein refers to bone containing less than 8% of its original mineral context. In some embodiments, fully demineralized contains about less than 8, 7, 6, 5, 4, 3, 2 and/or 1% of its original mineral content.

The expression "average length to average thickness ratio" as applied to the DBM fibers of the present application means the ratio of the longest average dimension of the fiber (average length) to its shortest average dimension (average thickness). This is also referred to as the "aspect ratio" of the fiber.

Fibrous, as used herein, refers to bone elements whose average length to average thickness ratio or aspect ratio of the fiber is from about 50:1 to about 1000:1. In some embodiments, average length to average thickness ratio or aspect ratio of the fiber is from about 50:1, 75:1, 100:1, 125:1, 150:1, 175:1, 200:1, 225:1, 250:1, 275:1, 300:1, 325:1, 350:1, 375:1, 400:1, 425:1, 450:1, 475:1, 500:1, 525:1, 550:1, 575:1, 600:1, 625:1, 650:1, 675:1, 700:1, 725:1, 750:1, 775:1, 800:1, 825:1, 850:1, 875:1, 900:1, 925:1, 950:1, 975:1 and/or 1000:1. In overall appearance, the fibrous bone elements can be described as bone fibers, threads, narrow strips, or thin sheets. Often, where thin sheets are produced, their edges tend to curl up toward each other. The fibrous bone elements can be substantially linear in appearance or they can be coiled to resemble springs. In some embodiments, the bone fibers are of irregular shapes including, for example, linear, serpentine or curved shapes. The bone fibers are demineralized, however some of the original mineral content may be retained when desirable for a particular embodiment. In various embodiments, the bone fibers are mineralized. In some embodiments, the fibers are a combination of demineralized and mineralized.

Non-fibrous, as used herein, refers to elements that have an average width substantially larger than the average thickness of the fibrous bone element or aspect ratio of less than from about 50:1 to about 1000:1. The non-fibrous bone elements are shaped in a substantially regular manner or specific configuration, for example, triangular prism, sphere, cube, cylinder and other regular shapes. By contrast, particles such as chips, shards, or powders possess irregular or random geometries. It should be understood that some variation in dimension will occur in the production of the elements of this application and elements demonstrating such variability in dimension are within the scope of this application and are intended to be understood herein as being within the boundaries established by the expressions "mostly irregular" and "mostly regular."

The term "bone fastener" or "bone fasteners" refer to multi-axial screws, uni-axial screws, fixed axis screws, sagittal adjusting screws, transverse sagittal adjusting screws, pedicle screws, uni-planar screws, facet screws, tissue penetrating screws, conventional screws, expanding screws, posts, tacs, cables, and/or sutures (e.g., wire/polymeric).

The bone implants, devices, kits and methods may be employed to treat spinal disorders such as, for example, degenerative disc disease, disc herniation, osteoporosis, spondylolisthesis, stenosis, scoliosis and other curvature abnormalities, kyphosis, tumor and fractures. The bone implants, devices, kits and methods may be employed with other osteal and bone related applications, including those associated with diagnostics and therapeutics. They may also be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The bone implants, devices, kits and methods may also be alternatively employed with procedures for treating the lumbar, cervical, thoracic, sacral and pelvic regions of a spinal column. They may also be used on animals, bone models and other non-living substrates, such as, for example, in training, testing and demonstration.

In various embodiments, the bone implant comprises a biodegradable mesh comprising poly(lactide-co-glycolide) (PLGA), polylactide (PLA), polyglycolide (PGA), D-lactide, D,L-lactide, L-lactide, D,L-lactide-co-ε-caprolactone, D,L-lactide-co-glycolide-co-s-caprolactone, L-lactide-co-ε-caprolactone or a combination thereof.

In some embodiments, a bone implant is provided comprising a mesh having hook-type polymer features embedded within the weave or knit of the mesh. The hooks provide flexibility in implant diameter and width and can be sealed and closed upon itself at varying diameters. Any fully absorbable material can be used to fabricate the mesh, such as, for example, absorbable polymers, such as, poly(lactic acid) (PLA), poly(glycolic acid) (PGA), poly(lactic-co-glycolic acid) (PLGA), polydioxanone (PDO), allogeneic collagen, xenogenic collagen, ceramic or a combination thereof. The mesh can be made from yarn that is monofilament or multi filament, and the mesh can be fabricated using knitting, weaving, non-woven, such as felted or point-bonded, or with additive manufacturing methods (e.g., 3D printing). The mesh has a pore size that is large enough so that cellular transport and formation of new bone is not impeded. However, the pore size is small enough to adequately contain graft material at an implant site. The bone implant can be various shapes and be provided with instruments designed to ease intraoperative use and assembly. The bone implant enables a streamline assembly. Customization of the bone implant diameter and width enables the bone implant to be used in a variety of bone fusion repair procedures that use a smaller graft size, such as, minimally invasive midline lumbar fusion, posterior cervical fusion and oral maxillofacial repair procedures.

In some embodiments, a mesh is provided that is formed as a bilayered envelope with two of the four sides closed during fabrication. The closed sides can be joined by, for example, ultrasonic welding, heat sealing or suturing. The two of the four sides being closed simplifies assembly by providing a preformed pocket configured for placement of bone material (e.g., bone graft).

In some embodiments, a device to hold the mesh while filling the mesh with bone material is provided. The device can be a tray and can be positioned in an upright configuration during placement of the bone material into the mesh. The tray can be a thermoform tray comprising a central trough. The tray may or may not be a part of a sterile packaging for the bone implant. The tray may also comprise projections or other features to clip and/or hold the bone implant in a desired spatial arrangement.

Bone Implant

Referring to FIGS. 1-4 and 6A to 7B, a bone implant 10 is provided that is customizable, self-sealing and is configured for sealing and enclosing a bone material 12, as described herein. The bone implant is configured to be cut and shaped in any size and diameter for a particular surgical site. The bone material described herein, can be fully or partially enclosed by the mesh 14.

The bone implant is configured, for example, for use in minimally invasive midline lumbar fusion, posterior cervical fusion and oral maxillofacial repair procedures. The bone implant may also be used in healing vertebral compression fractures, interbody fusion, additional minimally invasive procedures, posterolateral fusion procedures, correction of adult or pediatric scoliosis, treating long bone defects, osteochondral defects, ridge augmentation (dental/craniomaxillofacial, e.g. edentulous patients), beneath trauma plates, tibial plateau defects, filling bone cysts, wound healing, around trauma, contouring (cosmetic/plastic/reconstructive surgery), and others uses.

Figure 6C:
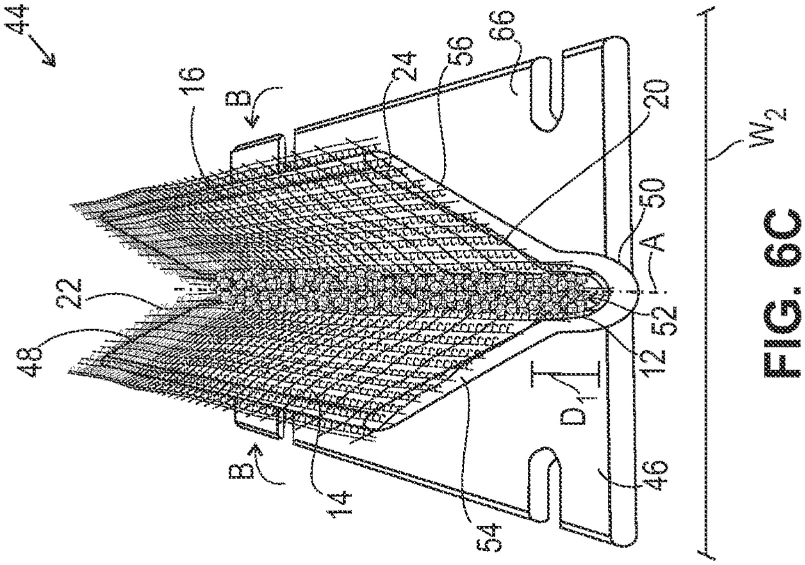
FIG. 6C illustrates a perspective view of the tray of FIG. 5A in a partially closed configuration and disposed with a bone implant comprising a mesh having a plurality of projections and a bone material.
Figure 6A:
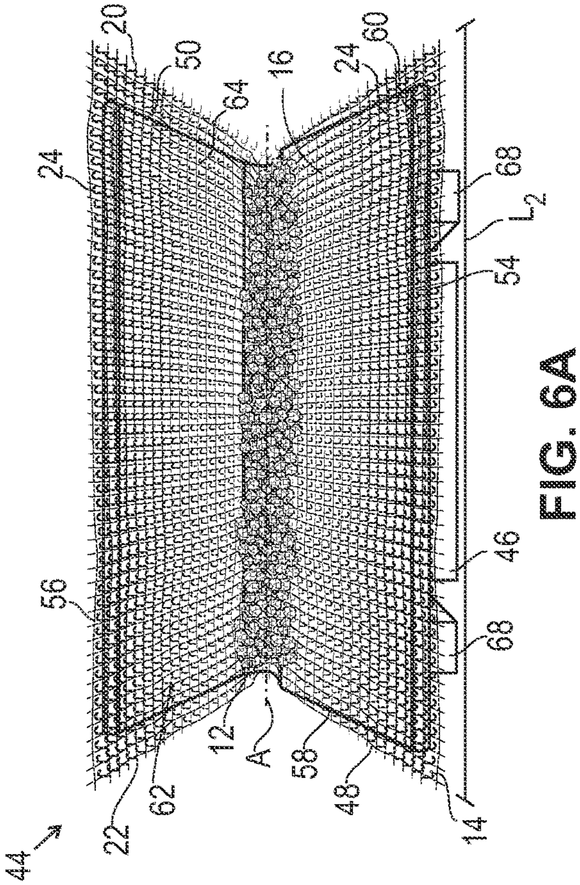
FIG. 6A illustrates a front view of the tray of FIG. 5A in an open configuration and disposed with a bone implant comprising a mesh having a plurality of projections and a bone material.
Figure 6B:
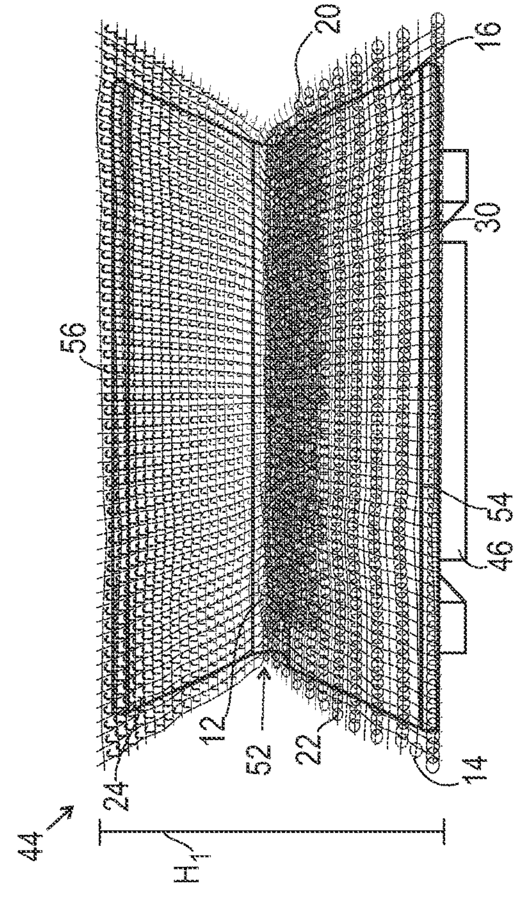
FIG. 6B illustrates a front view of the tray of FIG. 5A in an open configuration and disposed with a bone implant comprising a mesh having a plurality of projections, a plurality of recesses, and a bone material.

The bone implant comprises a mesh 14 having an inner surface 16 and an outer surface 18 opposing the inner surface. The inner surface is configured to receive the bone material when the inner surface of the mesh is in an open configuration, as shown in FIGS. 6A and 6B. The inner surface of the mesh comprises a distal end 20 and a proximal end 22, and a longitudinal axis A is disposed between proximal and distal ends, as shown in FIG. 6A.

The mesh can be made of yarn that is monofilament or multifilament, and the yarn can be knitted, woven, non-woven shape memory, felted, point-bonded, additive manufactured, such as 3-D printed or a combination thereof. A weave pattern can be selected to impart flexibility and stretchable characteristics to the mesh.

The mesh can have a weave density of from about 8 to about 400 filaments, such as fibers per inch. The mesh can have a weave density from about 8 to about 375 filaments fibers per inch, from about 8 to about 350 fibers per inch, from about 8 to about 300 fibers per inch, from about 8 to about 250 fibers per inch, from about 8 to about 200 fibers per inch, from about 20 to about 350 fibers per inch, from about 20 to about 300 fibers per inch, from about 20 to about 250 fibers per inch, from about 20 to about 200 fibers per inch, from about 50 to about 350 fibers per inch, from about 50 to about 300 fibers per inch, from about 50 to about 250 fibers per inch, from about 50 to about 200 fibers per inch, from about 100 to about 350 fibers per inch, from about 100 to about 300 fibers per inch, from about 100 to about 250 fibers per inch, or from about 100 to about 200 fibers per inch. The mesh can have a weave density from about 8, 10, 15, 20, 25, 30, 35, 40, 45, 50, 55, 60, 65, 70, 75, 80, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345 to about 350 fibers per inch.

The mesh can be absorbable and be made from a material, including, but not limited to at least one of poly(lactic acid) (PLA), poly(glycolic acid) (PGA), poly(lactic-co-glycolic acid) (PLGA), polydioxanone (PDO), allogeneic collagen, xenogenic collagen, ceramic or a combination thereof. The mesh when formed from an absorbable material may be substantially resorbed within 2 weeks, within 4 weeks, within 12 weeks, within 16 weeks, within 20 weeks, within 24 weeks, within 28 weeks, within 32 weeks, within 36 weeks, within 40 weeks, within 44 weeks, within 48 weeks, within 52 weeks or within any other suitable time frame.

The material and configuration of the mesh may be selected or adjusted based on desired release characteristics. Specific properties of the mesh that may be adjusted include thickness, permeability, porosity, strength, flexibility, and/or elasticity. In some embodiments, the thickness and porosity of the mesh may contribute to its strength, flexibility, and elasticity. In some embodiments, the mesh may be made of a squishy, moldable, sticky, and/or tacky material to facilitate placement and packing of the bone implant to a surgical site.

The average molecular weight of the polymer used to make the mesh can be from about 1,000 to about 10,000,000; or about 1,000 to about 1,000,000; or about 5,000 to about 500,000; or about 10,000 to about 100,000; or about 20,000 to 50,000 g/mol. In some embodiments, the molecular weight of the polymer is 1,000, 2,000, 3,000, 4,000, 5,000, 6,000, 7,000, 8,000, 9,000, 10,000, 15,000, 20,000, 25,000, 30,000, 35,000, 40,000, 45,000, 50,000, 55,000, 60,000, 65,000, 70,000, 75,000, 80,000, 85,000, 90,000, 95,000, 100,000, 125,000, 150,000, 175,000, 200,000, 225,000, 250,000, 275,000, 300,000, 325,000, 350,000, 375,000, 400,000, 425,000, 450,000, 475,000, 500,000, 525,000, 550,000, 575,000, 600,000, 625,000, 650,000, 675,000, 700,000, 725,000, 750,000, 775,000, 800,000, 825,000, 850,000, 875,000, 900,000, 925,000, 950,000, 975,000 and/or 1,000,000 Daltons.

The mesh may have varying degrees of permeability. It may be permeable, semi-permeable, or non-permeable. Permeability may be with respect to cells, to liquids, to proteins, to growth factors, to bone morphogenetic proteins, or other substances. The mesh may be 1 to about 30% permeable, from about 30 to about 70% permeable, or from about 70 to about 95% permeable. The mesh may be 1, 5, 10, 15, 20, 25, 30, 35, 40, 45, 50, 55, 60, 65, 70, 75, 80, 85, 90, 95, 96, 97, 98, or 99% permeable. In alternative embodiments, the mesh may comprise a substantially solid structure, such as a polymer structure with a chamber, or a spun cocoon.

The mesh can be a porous mesh such that fluid transfer and cell infiltration can occur so that osteoblasts can manufacture bone graft. The porous mesh can have a pore size of from about 1 micron to about 2000 microns, from about 1 micron to about 1500 microns, from about 1 micron to about 1000 microns, from about 1 micron to about 500 microns, from about 1 micron to about 250 microns, from about 100 micron to about 2000 microns, from about 150 to about 1500 microns, from about 200 to about 1000 microns, from about 250 to about 500 microns. In some embodiments, the pore size can be about 1, 10, 20, 50, 80, 100, 120, 150, 180, 200, 220, 250, 280, 300, 350, 400, 450, 500, 550, 600, 650, 700, 750, 800, 850, 900, 950, 1000, 1250, 1450, 1650, 1850, and/or 2000 microns.

Figure 7B:
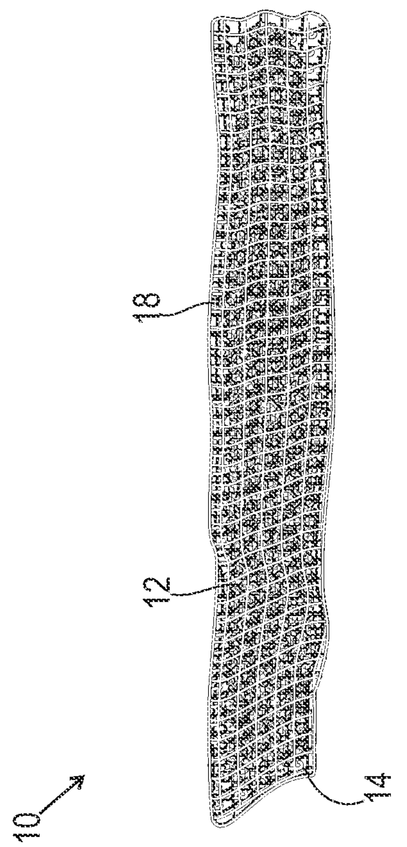
FIG. 7B illustrates a perspective view of the bone implant shown in 6A formed into a selected shape.
Figure 7A:
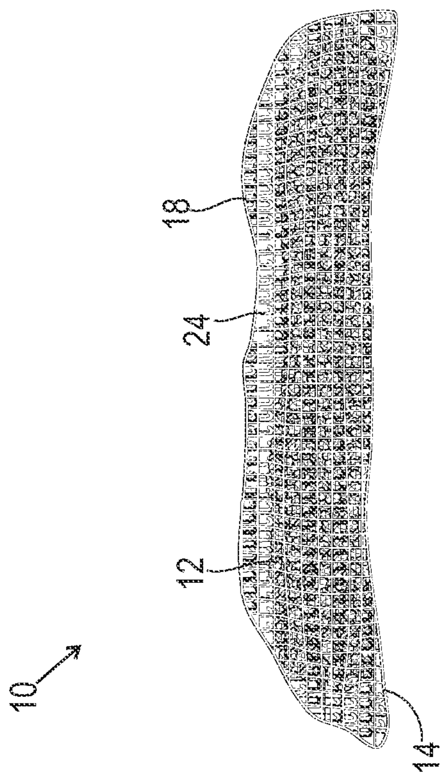
FIG. 7A illustrates a perspective view of the bone implant shown in 6A formed into a selected shape.

A plurality of projections, such as, for example, hooks 24 are disposed on or in at least a portion of the inner surface of the mesh. The hooks extend from at least the portion of the inner surface of the mesh, and are configured to engage a section of the inner surface of the mesh or a section of the outer surface of the mesh or both sections of the inner and outer surfaces of the mesh when the mesh is in a closed configuration so as to enclose the bone material (e.g., closed configuration is shown in FIGS. 7A and 7B).

Each of the hooks include a proximal end 26 and a distal end 28, as shown in FIG. 1. The distal end is fixed on or in at least a portion of the inner surface of the mesh and the proximal end engages one or a plurality of projections that are disposed on or in at least a portion of an opposing inner surface of the mesh, or a section of the mesh that comprises the weave or a plurality of recesses disposed in or on the mesh, as described herein. The hooks can be made from the same material as the mesh or a different material than the mesh and can be interwoven in the weave of the mesh. Alternatively, the hooks are formed from the same material as the mesh and are disposed on the inner surface of the mesh. The hooks can also be added to the entire inner surface of the mesh or a portion of the inner surface of the mesh after the mesh is manufactured via a coating, 3D printing and/or screen printing.

The plurality of projections can also be teeth, spikes, barbs, protuberances, prongs, clips, spurs, quills, pins, or a combination thereof. These projections can contact the opposing surface of the mesh and seal the mesh on contact with the opposing surface of the mesh. In some embodiments, the density of the plurality of projections can be from about 1 to about 500 projections per inch, from about 1 to about 400 projections per inch, from about 1 to about 350 projections per inch, from about 1 to about 300 projections per inch, from about 1 to about 250 projections per inch, from about 1 to about 200 projections per inch, from about 1 to about 150 projections per inch, from about 1 to about 100 projections per inch, or from about 1 to about 50 projections per inch. In some embodiments, the density of the plurality of projections can be from about 1, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 to about 500 projections per inch. The density of the plurality of projections may be uniform throughout the inner surface of the mesh or may not be uniform.

Each of the plurality of projections may have a selected length $L_1$ of, in some embodiments, from about 0.001 millimeters (mm) to about 4 mm, from about 0.005 mm to about 3 mm, or from about 0.01 mm to about 2 mm. Each of the plurality of projections may have a selected length of from about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9 to about 4 mm. Each of the plurality of projections may have the same or different lengths.

Each of the plurality of projections may have a selected width $W_1$ of, in some embodiments, from about 0.001 to about 1 mm, from about 0.003 mm to 0.05 mm, or from about 0.005 mm to about 0.08 including or excluding a proximal end comprising a hook portion. Each of the plurality of projections may have, in some embodiments, a selected width of from about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, to about 1 mm including or excluding a proximal end comprising a hook portion. Each of the plurality of projections may have the same or different widths.

Figure 2:
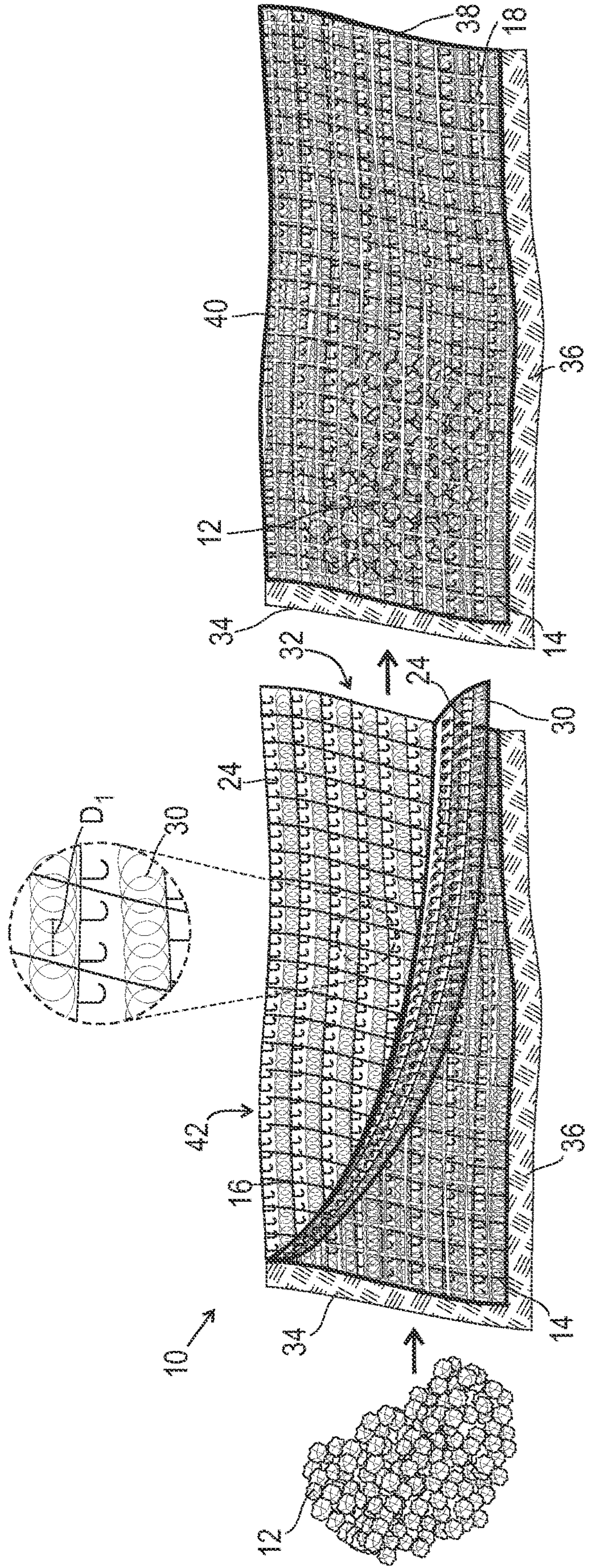
FIG. 2 illustrates a perspective view of a bone implant for enclosing bone material, similar to the bone implant of FIG. 1. The bone implant further comprises a plurality of recesses in or on the section of the inner surface configured to mate with the plurality of projections of the inner surface.

The projections are configured for mating engagement with opposing projections. For example, a plurality of projections fixed on or in at least a portion of the inner surface of the mesh, slidably engage via their proximal end with proximal ends of a plurality of projections or gaps between a plurality of projections that are disposed on or in at least a portion of an opposing inner surface of the mesh (FIG. 1 and FIG. 3), or a section of the mesh that comprises the weave or a plurality of recesses 30 disposed in or on the mesh (FIG. 2). In some embodiments, the opposing plurality of projections slide and matingly engage in 2 projections to 1 projection engagement, in 3 projections to 1 projection engagement, in 4 projections to 2 projections engagement and/or 1 projection to 1 projection engagement.

The plurality of projections is flexible so as to facilitate mating engagement, as described above. The flexibility of the plurality of projections is measured by tensile elasticity or its modulus of elasticity. The plurality of projections, in some embodiments, have a modulus of elasticity of about $1\times10^2$ to about $6\times10^5$ dyn/cm$^2$, or $2\times10^4$ to about $5\times10^5$ dyn/cm$^2$, or $5\times10^4$ to about $5\times10^5$ dyn/cm$^2$.

The mating engagement of the projections to opposing projections and/or recesses may have an attachment strength such as a sheer strength, lateral sheer and/or peel strength of about 20 to about 400 Newtons (N), about 50 to about 350 N, about 50 to about 300 N, about 75 to about 300 N, about 75 to about 200 N, or about 100 to about 150 N. The mating engagement of the projections to opposing projections and/or recesses may have an attachment strength such as a sheer strength, lateral sheer and/or peel strength of from about 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, to about 300 N.

Figure 3:
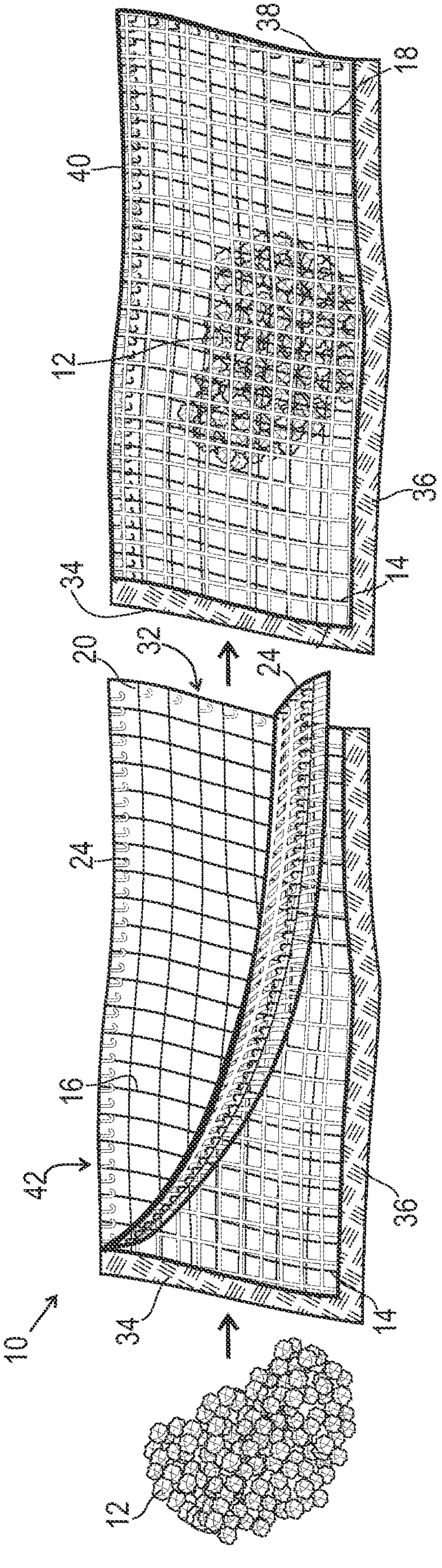
FIG. 3 illustrates a perspective view of a bone implant for enclosing bone material, similar to the bone implant of FIG. 1. The plurality of projections are alternatively disposed at discrete regions on or in the inner surface.

In FIGS. 1-3 the left side illustrates an open or partially open configuration to the mesh and the bone material 12 is being filled into the mesh. FIGS. 1-3 the right side illustrates a closed configuration to the mesh and the bone material 12 is enclosed by the mesh.

In some embodiments, as shown in FIGS. 1, 5A, 5C, 6A and 6B, the plurality of projections is disposed on or in the entire inner surface of the mesh. In some embodiments, the plurality of projections are disposed in or on discrete regions of the inner surface of the mesh, as shown in FIG. 3. For example, in FIG. 3, the plurality of projections is disposed adjacent to edges of the mesh. The mesh is sealed by hand or machine by bringing opposing projections together at the discrete regions and applying pressure to those regions to seal the mesh and enclose or partially enclose the bone material inside the mesh as shown on the right side of FIG. 3.

As shown in FIGS. 2 and 6B, a section of the inner surface of the mesh can also include the plurality of recesses configured to mate with the plurality of projections. The plurality of recesses can be loops, indents, holes, grooves, tabs, grommets, or channels that are fabricated from the yarn of the mesh in or on a section of the inner or outer surface of the mesh. The plurality of recesses may also be defined by voids created by a weave of the yarn.

The density of the plurality of recesses can be from about 1 to about 500 recesses per inch, from about 1 to about 400 recesses per inch, from about 1 to about 350 recesses per inch, from about 1 to about 300 recesses per inch, from about 1 to about 250 recesses per inch, from about 1 to about 200 recesses per inch, from about 1 to about 150 recesses per inch, from about 1 to about 100 recesses per inch, or from about 1 to about 50 recesses per inch. The density of the plurality of recesses can be from about 1, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 or 500 recesses per inch. The density of the plurality of recesses may be uniform throughout the inner surface of the mesh or may not be uniform.

The plurality of recesses may each have a selected diameter Di, as shown in FIG. 2, such as, for example, 0.001 mm to about 5 mm, from about 0.005 mm to about 4 mm, from about 0.05 mm to about 3 mm, from about 0.05 mm to about 2 mm, or from about 0.5 mm to about 1 mm. The diameter of each of the plurality of recesses may be 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.09, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 4, or 5 mm.

In some embodiments, the plurality of projections can be hooks and the plurality of recesses can be loops, similar to Velcro®. Alternatively, the hook and loop mating is absorbable Velcro®.

The plurality of projections and the plurality of recesses can be formed in such a manner that they are located in different planes, portions and/or sections of the inner surface and/or the outer surface of the mesh. The plurality of projections and/or the plurality of recesses may be directed in different planes relatively to one another, or they may be located in planes disposed at different levels relative to that of a section or portion of the inner surface or the outer surface on which they are disposed. The plurality of projections and/or recesses can be disposed in or on the inner surface of the mesh in patterns, such as, clusters, strips, zig-zags, and/or waves.

The mesh is foldable in a closed configuration so as to enclose the bone material within the inner surface of the mesh. The mesh can be manually or mechanically folded either during manufacture or prior to a surgical procedure. In some embodiments, the inner surface of the mesh may comprise a fold line extending from a distal end to a proximal end of the inner surface. The fold line is configured to form a compartment to receive the bone material. The mesh is also configured to roll the section of the inner surface over the bone material to enclose the bone material, as shown in FIG. 7B.

As shown in FIGS. 1 to 3, a compartment 32 is provided that extends from the distal end to the proximal end of the inner surface of the mesh. The compartment is configured to receive the bone material. In some embodiments, the plurality of projections and/or the plurality of recesses are disposed on the entire inner surface including the location that makes up the compartment, as shown in FIGS. 1 and 2. In some embodiments, the location of the inner surface that makes up the compartment does not have any of the plurality of the projections, as shown in FIG. 3. Therefore, in some embodiments, the mesh may have a compartment without any projections, which is a filling space for the bone material to be disposed therein.

As shown in FIGS. 1-3, the outer surface of the mesh has a first edge 34 and a second edge 36. The first edge is adjacent to the second edge to form a seal with the inner surface of the mesh. The outer surface includes a third edge 38 and a fourth edge 40. The first edge is adjacent to the second edge, the second edge is adjacent to the third edge, and the fourth edge is adjacent to the first edge. Each of the edges are configured to form a seal with the inner surface, and the third edge and the fourth edge can be sealed by engagement of the plurality of projections and/or the plurality of recesses. For example, as shown in FIG. 3, the plurality of projections are disposed in discrete regions of the inner surface, such as on edges of the inner surface to seal the third and fourth edges of the outer surface to the inner surface, thereby placing the mesh in a closed configuration. In the closed configuration, the bone material becomes enclosed within the inner surface/compartment of the mesh. At least the first and second edges are sealed by ultrasonic welding, heat sealing or suturing. However, the third and/or fourth surface can also be sealed by these techniques.

The edges of the mesh form a pocket or envelope shape that includes the compartment configured for disposal of the bone material. The pocket or envelope shape includes an opening 42 that is created by the sealed first and second edges. The opening can be V-shaped. The opening can also be formed by sealing of the first, second and third edges.

In some embodiments, the mesh can fully enclose the bone material, where the mesh surrounds the entire bone material (e.g., bone particles, bone cement, etc.) to fully enclose it. In some embodiments, the mesh can partially enclose the bone material (e.g., bone particles, bone cement, etc.), where the mesh surrounds a portion of the bone material leaving a portion of the bone material that is not enclosed by the mesh.

The bone material of the bone implant can comprise fully demineralized bone fibers and surface demineralized bone chips. The bone material may also comprise fibers, powder, chips, triangular prisms, spheres, cubes, cylinders, shards or other shapes having irregular or random geometries. These can include, for example, "substantially demineralized," "partially demineralized," or "fully demineralized" cortical and/or cancellous bone. These also include surface demineralization, where the surface of the bone construct is substantially demineralized, partially demineralized, or fully demineralized, yet the body of the bone construct is fully mineralized.

In some embodiments, the bone implant is configured to self-seal and to seal and enclose the bone material via chemical fusion, heat treatment, self-fusing materials, self-adhering materials, adhesives, or a combination thereof. In some embodiments, adhesives that can be used include, but are not limited to cyanoacrylates (such as histoacryl, B Braun, which is n-butyl-2 cyanoacrylate; or Dermabond, which is 2-octylcyanoacrylate), epoxy-based compounds, dental resin sealants, dental resin cements, glass ionomer cements, polymethyl methacrylate, gelatin-resorcinol-formaldehyde glues, collagen-based glues, inorganic bonding agents such as zinc phosphate, magnesium phosphate or other phosphate-based cements, zinc carboxylate, L-DOPA (3,4-dihydroxy-L-phenylalanine), proteins, carbohydrates, glycoproteins, mucopolysaccharides, other polysaccharides, hydrogels, protein-based binders such as fibrin glues and mussel-derived adhesive proteins, and any other suitable substance. In some embodiments, the bone implant is sealable via mechanical means such as, for example, zippers, sutures, staples, pins, snaps, clips or a combination thereof.

Kit

Referring to FIGS. 5A to 6C, a kit 44 is provided for filling bone material in a bone implant, such as implant 10 described in FIGS. 1-3 and 6A to 7B. The kit is used to fill the bone implant with bone material 12 when the mesh 14 is in an open or partially open configuration, as shown in FIGS. 1-3 (left side) and 6A to 6C. The kit can be employed with bone implants that are configured for minimally invasive midline lumbar fusion, posterior cervical fusion and oral maxillofacial repair procedures. The kit can also be employed with bone implants used in healing vertebral compression fractures, interbody fusion, additional minimally invasive procedures, posterolateral fusion procedures, correction of adult or pediatric scoliosis, treating long bone defects, osteochondral defects, ridge augmentation (dental/craniomaxillofacial, e.g. edentulous patients), beneath trauma plates, tibial plateau defects, filling bone cysts, wound healing, around trauma, contouring (cosmetic/plastic/reconstructive surgery), and others.

The kit comprises bone implant 10, described herein, comprising mesh 14 that is configured to receive bone material 12 when the inner surface of the mesh is in an open configuration, as shown in FIGS. 1-3 (left side) and 5A-5C. The kit includes the plurality of projections 24 that are disposed on or in at least a portion of the inner surface 16 of the mesh, configured to engage a section of the inner surface of the mesh or a section of the outer surface 18 of the mesh, or both sections of the inner and outer surfaces of the mesh in a closed configuration so as to enclose the bone material, as shown in FIGS. 1-3 (right side) and 6A-6B.

The kit further includes a tray 46 having a proximal end 48 and a distal end 50. The tray can be disposed in an upright vertical or a horizontal configuration, and is configured to hold the bone implant in place during filling of the mesh with bone material. The tray is also configured to be movable and foldable in an open (FIG. 6A) and closed (FIG. 5A) configuration to fill the bone implant and place the bone implant in a closed configuration. The tray can be made from a metal, thermoform, or a polymer, such as, polyurethane, polyurea, polyether (amide), PEBA, thermoplastic elastomeric olefin, copolyester, and styrenic thermoplastic elastomer, steel, aluminum, stainless steel, titanium, nitinol, metal alloys with high non-ferrous metal content and a low relative proportion of iron, carbon fiber, glass fiber, plastics, ceramics or a combination thereof.

When the tray is made from a thermoform material, the thermoform material may be acrylonitrile butadiene styrene (ABS), polymethyl methacrylate (PMMA, Acrylic, or Plexiglass®), high density polyethylene (HDPE), high impact polystyrene (HIPS), KYDEX™ (PMMA/polyvinyl chloride (PVC) blend), polycarbonate (PC), polyetherimide (PEI or Ultem®), polyethylene terephthalate glycol (PETG), polypropylene (PP), polyvinyl chloride (PVC), thermoplastic polyolefin (TPO).

The tray may also be made from memory shape polymers including, but not limited to, polyethers, polyacrylates, polyamides, polysiloxanes, polyurethanes, polyethers amides, polyurethane/ureas, polyether esters, polynorborene, cross-linked polymers such as cross-linked polyethylene and cross-linked poly(cyclooctene), inorganic-organic hybrid polymers, and copolymers such as urethane/butadiene copolymers, styrene-butadiene copolymers. Memory shape alloys include, but are not limited to TiNi, CuZnAl, and FeNiAl alloys.

Longitudinal axis A and a longitudinal recess 52 are disposed between proximal and distal ends. The longitudinal recess is configured to receive the mesh in the open configuration to allow filling of the bone material into the bone implant. The recess of the tray forms a slot for receiving the mesh and the recess forms a fill zone for the bone material to be deposited in. The longitudinal recess may be centrally located in the tray. The longitudinal recess can alternatively be offset or there may be a plurality of longitudinal recesses disposed in the tray for placement of multiple bone implants and/or mesh.

The longitudinal recess can be a channel, a trough, slot, a groove or grooves, an indent or indents or a combination thereof. The longitudinal recesses can additionally comprise fastening elements, such as, for example, projections, clips, hooks, ridges, and/or snaps for fixing the bone implant and/or mesh within the longitudinal recess. The longitudinal recess can have a selected depth Di as shown in FIG. 6C, such as, for example, about 1 to about 14 mm, from about 1 to about 10 mm, from about 1 to about 8 mm, or from about 1 to about 6 mm. The depth can be from about 1, 2, 3, 4, 5, 6, 7, 8, 9, 10, 11, 12, 13 or 14 mm.

A first tray section 54 and a second tray section 56 are parallel to each other and adjacent to the longitudinal recess. The first tray section and the second tray section are movable and configured to translate in an upward direction, as shown by arrows B in FIG. 6C, to place the tray and/or the bone implant in a closed configuration, and in a downward direction, as shown by arrows C in FIG. 5A, to place the tray and/or the bone implant in an open configuration. The first tray section comprises a first end 58 and a second end 60, and the second tray section comprises a first end 62 and a second end 64. The first and second tray section first ends are on the proximal end of the tray and the first and second tray section second ends are on the distal end of the tray. The first and second tray sections are attached to a base 66 and the base may comprise feet 68. In some embodiments, the tray is flat without a base and the first and second tray sections are fixed and are not movable.

When combined, the first and second tray sections form an angle when in the open configuration, in a range of about 20 to about 180°, from about 20 to about 160°, from about 20 to about 140°, from about 20 to about 90°, from about 20 to about 45°, from about 45 to about 160°, from about 45 to about 120°, from about 45 to about 90°, from about 60 to about 180°, from about 60 to about 120°, from about 60 to about 90°, from about 90 to about 180°, from about 90 to about 120°, or from about 120 to about 180°. The angle when in the open configuration can be from about 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175 to about 180°. The first and second tray sections can be manually moved by a user to set the tray sections at a desired angle. In some embodiments, the tray is tension set at the selected angle.

In some embodiments, the first and second tray sections can include a seal surface disposed on outer edges of the tray sections. The seal surface is configured to provide additional grip on a surface of the tray sections to further secure the bone implant in place during bone material filling. The seal surface can be made from a rubber and/or a plastic, as those described herein.

The tray can have a selected length $L_2$ shown in FIG. 6A, such as, from about 3 inches to about 20 inches, from about 3 inches to about 15 inches, from about 3 inches to about 10 inches, from about 5 inches to about 20 inches, from about 5 inches to about 15 inches, from about 5 to about 10 inches, from about 10 inches to about 20 inches, from about 10 inches to about 20 inches, or from about 15 inches to about 20 inches. The length of the tray can be from about 1, 2, 3, 4, 5, 6, 7, 8, 9, 10, 11, 12, 13, 14, 15, 16, 17, 18, 19 or 20 inches.

The tray can have a selected width $W_2$ shown in FIG. 6C, such as, for example, from about 3 to about 12 inches, from about 3 to about 10 inches, from about 3 to about 8 inches, from about 3 to about 6 inches, from about 5 to about 12 inches, from about 5 to about 10 inches, from about 5 to about 8 inches, from about 8 to about 12 inches, or from about 8 to about 10 inches. The tray can have a width of about 3, 4, 5, 6, 7, 8, 9, 10, 11, or 12 inches.

The tray can have a selected height Hi shown in FIG. 6B, when in a horizontal position, such as, for example, from about 4 inches to about 12 inches, from about 4 inches to about 10 inches, from about 4 inches to about 8 inches, from about 6 inches to about 12 inches, from about 8 inches to about 10 inches, or from about 10 inches to about 12 inches. The height of the tray can be from about 4, 5, 6, 7, 8, 9, 10, 11, or 12 inches.

In some embodiments, the tray can include visual indicia, such as, for example, markings that enable a user to measure defined volumes of material being placed into the mesh. In some embodiments, the tray can include length and/or volume markings to assist in filling the mesh.

In various embodiments, the kit may include additional parts along with the bone implant and tray such as wipes, needles, measuring devices, and syringes. The kit may include the mesh in a first compartment. The second compartment may include a vial holding the bone material, diluent and any other instruments needed for the localized implant delivery. A third compartment may include the tray for filling the bone implant. A fourth compartment may include gloves, drapes, wound dressings and other procedural supplies for maintaining sterility of the implanting process, as well as an instruction booklet, which may include a chart that shows how to implant the bone implant. A fifth compartment may include additional needles, measuring devices, fasteners, and/or sutures. Each tool may be separately packaged in a plastic pouch that is radiation sterilized. A sixth compartment may include an agent for radiographic imaging. A cover of the kit may include illustrations of the implanting procedure and a clear plastic cover may be placed over the compartments to maintain sterility.

Mesh

The mesh of the instant application may be made from woven threads that are configured to allow ingrowth of cells while also retaining the bone material within the compartment of the bone implant. The threads of the mesh may have a predetermined thickness of about 0.01 mm to about 2.0 mm, about 0.05 mm to about 1.0 mm, or about 0.1 to about 0.5 mm. The thickness of the threads may be uniform along the length of each thread, or varied across the length of each thread. In some embodiments, some threads have a greater thickness than other threads. The threads may be sized to allow for customizable pore sizes between the threads. In some embodiments, the bone implant is configured to facilitate transfer of substances and/or materials surrounding the surgical site. Upon implantation to a surgical site, the bone implant may participate in, control, or otherwise adjust, or may allow penetration of the mesh by surrounding materials, such as cells or tissue.

The mesh may be sized according to the needs of a particular application. For example, the mesh may include dimensions between about 1 mm to about 100 mm in diameter. In some embodiments, the mesh includes a diameter of about 5 mm, 10 mm, 15 mm, 20 mm, 25 mm, 30 mm, 35 mm, 40 mm, 45 mm, 50 mm, 55 mm, 60 mm, 65 mm, 70 mm, 75 mm, 80 mm, 85 mm, 90 mm, 95 mm, or 100 mm. In some embodiments, the mesh includes a length or depth between about 0.1 cm to about 10 cm. In some embodiments, the mesh includes a length or depth of about 1 cm, 2 cm, 3 cm, 4 cm, 5 cm, 6 cm, 7 cm, 8 cm, 9 cm, or 10 cm.

In some embodiments, the mesh can have selected dimensions, such as, for example, a diameter of 0.5 cm and a length of 0.1 cm, providing a volume of 0.02 cc. In other embodiments, the mesh can have a diameter of 1 cm and a length of 1 cm, providing a volume of 0.79 cc. In yet other embodiments, a mesh bag has a diameter of 1.5 cm and length of 3 cm, providing a volume of 5.3 cc.

The shape, mesh size, thickness, and other structural characteristics, of the mesh, for example, architecture, may be customized for the desired application. For example, to optimize cell or fluid migration through the mesh, the pore size may be optimized for the viscosity and surface tension of the fluid or the size of the cells. For example, pore sizes between threads on the order of approximately 100-200 μm may be used if cells are to migrate through the mesh. In other embodiments, wave-shaped threads may be extruded to have larger peaks and crests and the size of the pores may be larger. For example, in some embodiments, the pore size between threads may be about 0.1 mm to about 5 mm, about 0.5 mm to about 3 mm, or about 1 mm to about 2 mm. Mesh size may be controlled by physically weaving strands and by controlling the thickness of threads.

The mesh may have varying degrees of permeability across its surface. It may be permeable, semi-permeable, or non-permeable. Permeability may be with respect to cells, to liquids, to proteins, to growth factors, to bone morphogenetic proteins, or other. In further embodiments, the material may be braided.

The mesh may have any suitable custom configuration. For example, the mesh can have a variety of shapes, such as, for example, a ring, a cylinder, a cage, a rectangular shape, a suture-like wrap, a continuous tube, or other configurations. The mesh may be formed as a thin tube designed to be inserted through catheters or an introducer tube; a rectangular shape designed to fit adjacent to spinal processes for posterolateral spine fusion; a cube; a rectangular prism like structure designed to fit between vertebral bodies or within cages for interbody spinal fusion; a tube-like shape; relatively flat shapes; rectangular shapes; structures pre-shaped to fit around various implants (e.g., dental, doughnut with hole for dental implants); or relatively elastic ring-like structures that will stretch and then conform to shapes (e.g., rubber band fitted around processes).

Additionally, in some embodiments, the flexible character of the mesh allows for the mesh to be manipulated into a plurality of compartments. For example, in a tubular embodiment, the tube may be formed into a plurality of compartments by tying a cord around the tube at one or more points, or by other suitable mechanism such as crimping, twisting, knotting, stapling, or sewing.

In certain embodiments, a bone void can be filled by the mesh containing bone material. A compartment within mesh can be at least partially filled with a bone repair substance. In various embodiments, at least partially filled as used herein, can mean that a percentage of the volume of a compartment or hollow interior region is at least 70% occupied, at least 75% occupied, at least 80% occupied, at least 85% occupied, at least 90% occupied, at least 95% occupied, or 100% occupied. The mesh can be inserted into an opening in the defect until the defect is substantially filled. In various embodiments, substantially filled, as used herein, can mean that a percentage of the volume of a defect is at least 70% occupied, at least 75% occupied, at least 80% occupied, at least 85% occupied, at least 90% occupied, at least 95% occupied, or 100% occupied.

In some embodiments, the mesh may be labeled. Such labeling may be done in any suitable manner and at any suitable location on the mesh. In some embodiments, labeling may be done by using a silk screen printing, using an altered weaving or knotting pattern, by using different colored threads, or other means. The labeling may indicate information regarding the mesh. Such information might include a part number, donor ID number, number, lettering or wording indicating order of use in the procedure or implant size, etc. In some embodiments, the mesh can be a specific color to help provide the correct orientation of the mesh prior to or during filling and to confirm that the plurality of projections and/or plurality of recesses of the mesh are oriented to optimize their engagement. In some embodiments, a portion of the mesh or the entire mesh is colored blue, purple, pink, orange, yellow, green, or red.

Figure 4:
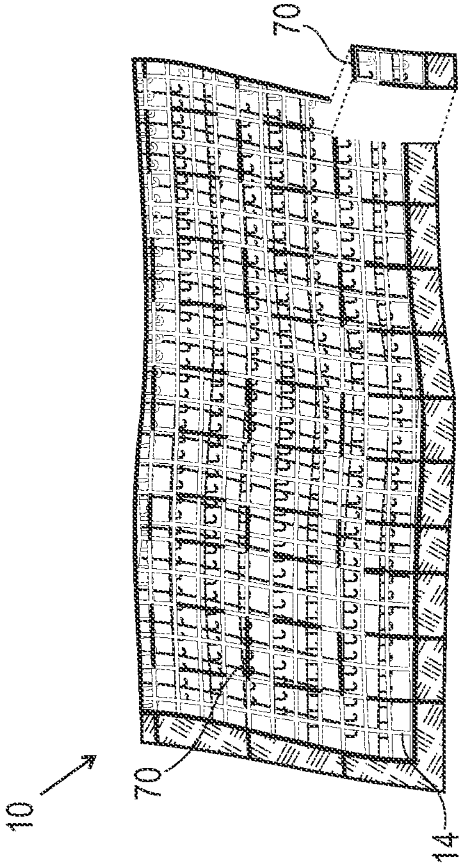
FIG. 4 illustrates a perspective view of a bone implant for enclosing bone material, similar to the bone implant of FIG. 1. The mesh comprises score lines or separation assist lines so that a user can easily tear and/or size the mesh prior to or after filling.

In some embodiments, the mesh can be pre-cut, perforated and/or notched so that a user can easily cut, tear and/or size the mesh prior to or after filling. In some embodiments, as shown in FIG. 4, the mesh can have score lines or separation assist lines 70 for easy tearing of the mesh. In this manner, the mesh may be used either in its entirety at a surgical site, or may be manipulated by a user to separate the mesh into multiple smaller pieces, some or all of which may be used, at a single surgical site or at multiple different surgical sites. The score lines or separation assist lines afford the user an ability to conveniently adjust the size of the mesh based upon the size of the defect to be filled or other factors noted in the operational field, which can help to assure that a mesh volume of an appropriate size is used. For example, this can help to assure that the use of an inappropriately oversized mesh is avoided, e.g. one which would be packed into a defect under too much compression thus potentially leading to an undesired increase in the spatial density or concentration of an osteoconductive and/or osteoinductive bone material in the mesh, and/or creating too much compression on surrounding soft or hard tissues, or that the use of an inappropriately undersized mesh is avoided, e.g. one that would be packed into a defect too loosely. In some embodiments, the mesh can be filled with bone material, sealed closed, and then torn at the score lines or separation assist lines. Alternatively, the mesh can be torn first at the score lines or separation assist lines, filled with bone material, and then sealed.

In some embodiments, a portion of the mesh or the entire mesh can be pre-folded and/or contain bent sections that enable a user to create pre-selected shapes and/or patterns from the mesh. In some embodiments, the mesh can be pre-folded and/or contain bent sections that are configured into a box or tube shape.

The mesh may comprise a penetrable material at a first compartment configured for placement adjacent bone and a substantially impenetrable material at a second compartment configured for placement adjacent soft tissue. For example, the pore size between the threads at a first region of the mesh may be sized large enough to allow cell migration through the mesh, but the pore size between the threads at a second region of the may be sized small enough (or may include a lack of pores altogether) to prevent cell migration. Alternatively, the material of the mesh may have a uniform configuration such that adjacent compartments may have substantially identical characteristics. By way of example only, the mesh may have a porous surface that is positioned adjacent bone, and a separate or opposite surface that has a generally impenetrable surface that is positioned adjacent soft tissue. Alternatively, the mesh may have one compartment that comprises a porous material, and a second compartment that comprises a substantially impenetrable material.

For either single and multi-compartment bone implants, the mesh may be closed after filling substances. Accordingly, the bone implant may be provided in an unfilled, unsealed state. After a substance for delivery is placed in the bone implant, the mesh of the bone implant may be permanently or temporarily closed by the plurality of projections and/or the plurality of recesses. Further, temporary closure may be by tying, fold lock, cinching, or other means. A temporarily closed bone implant can be opened without damaging the mesh during surgical implantation to add or remove substances in the bone implant.

In some embodiments, biological attachment may be via mechanisms that promote tissue ingrowth such as by a porous coating or a hydroxyapatite-tricalcium phosphate (HA/TCP) coating. Generally, hydroxyapatite bonds by biological effects of new tissue formation. Porous ingrowth surfaces, such as titanium alloy materials in a beaded coating or tantalum porous metal or trabecular metal may be used and facilitate attachment at least by encouraging bone to grow through the porous implant surface. These mechanisms may be referred to as biological attachment mechanisms. In some embodiments, the bone implant may be attached to a tissue structure through a wrap, a suture, a wire, a string, an elastic band, a cable or a cable tie, or a combination thereof or another fastener.

In other embodiments, suitable materials that form the mesh of the bone implant include natural materials, synthetic polymeric resorbable materials, synthetic polymeric non-resorbable materials, and other materials. Natural mesh materials include silk, extracellular matrix (such as DBM, collagen, ligament, tendon tissue, or other), silk-elastin, elastin, collagen, and cellulose. Synthetic polymeric resorbable materials include poly(lactic acid) (PLA), poly(glycolic acid) (PGA), poly(lactic acid-glycolic acid) (PLGA), polydioxanone, PVA, polyurethanes, polycarbonates, and others.

In various embodiments, the mesh comprises a polymer matrix. In some embodiments, DBM fibers and/or DBM powder are suspended in the polymer matrix to facilitate transfer of cells into and out of the mesh bag to induce bone growth at the surgical site. In other embodiments, the mesh further comprises mineralized bone fibers suspended in a polymer matrix. In some embodiments, the DBM powder is suspended in the polymer matrix between the DBM fibers and the mineralized bone fibers. In some embodiments, the DBM powder is suspended between the DBM fibers in the polymer matrix so as to reduce and/or eliminate gaps that exist between the fibers. In some embodiments, the DBM powder is suspended between the DBM fibers in the polymer matrix to improve osteoinductivity for facilitating bone fusion, for example, interspinous process fusion.

In some embodiments, the polymer matrix comprises a bioerodible, a bioabsorbable, and/or a biodegradable biopolymer that may provide immediate release or sustained release. Examples of suitable sustained release biopolymers include, but are not limited to, poly(alpha-hydroxy acids), poly(lactide-co-glycolide) (PLGA), polylactide (PLA), polyglycolide (PG), polyethylene glycol (PEG), conjugates of poly(alpha-hydroxy acids), poly(orthoester) s (POE), polyaspirins, polyphosphagenes, collagen, starch, pre-gelatinized starch, hyaluronic acid, chitosans, gelatin, alginates, albumin, fibrin, vitamin E compounds, such as alpha tocopheryl acetate, d-alpha tocopheryl succinate, D,L-lactide, or L-lactide, caprolactone, dextrans, vinylpyrrolidone, polyvinyl alcohol (PVA), PVA-g-PLGA, PEGT-PBT copolymer (polyactive), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate), or combinations thereof. mPEG and/or PEG may be used as a plasticizer for PLGA, but other polymers/excipients may be used to achieve the same effect. mPEG imparts malleability to the polymer. In some embodiments, these biopolymers may also be coated on the mesh to provide a desired release profile or ingrowth of tissue. In some embodiments, the coating thickness may be thin, for example, from about 5, 10, 15, 20, 25, 30, 35, 40, 45 or 50 microns to thicker coatings 60, 65, 70, 75, 80, 85, 90, 95, 100 microns to delay release of the substance from the bone implant. In some embodiments, the range of the coating on the mesh ranges from about 5 microns to about 250 microns or 5 microns to about 200 microns.

In some embodiments, various components of the mesh comprises poly(lactide-co-glycolide) (PLGA), polylactide (PLA), polyglycolide (PGA), D-lactide, D,L-lactide, L-lactide, D,L-lactide-co-ε-caprolactone, D,L-lactide-co-glycolide-co-ε-caprolactone, L-lactide-co-ε-caprolactone or a combination thereof.

In some embodiments, the mesh further comprises bone morphogenic proteins (BMPs), growth factors, antibiotics, angiogenesis promoting materials, bioactive agents or other actively releasing materials.

The mesh may be used to deliver a substance comprising any suitable biocompatible material. In specific embodiments, the mesh may be used to deliver surface demineralized bone chips, optionally of a predetermined particle size, fully demineralized bone fibers, optionally pressed, and/or allograft. For embodiments where the substance is a biologic, the substance may be autogenic, allogenic, xenogenic, or transgenic. Other suitable materials that may be positioned in the mesh include, for example, protein, nucleic acid, carbohydrate, lipids, collagen, allograft bone, autograft bone, cartilage stimulating substances, allograft cartilage, TCP, hydroxyapatite, calcium sulfate, polymer, nanofibrous polymers, growth factors, carriers for growth factors, growth factor extracts of tissues, DBM, dentine, bone marrow aspirate, bone marrow aspirate combined with various osteoinductive or osteoconductive carriers, concentrates of lipid derived or marrow derived adult stem cells, umbilical cord derived stem cells, adult or embryonic stem cells combined with various osteoinductive or osteoconductive carriers, transfected cell lines, bone forming cells derived from periosteum, combinations of bone stimulating and cartilage stimulating materials, committed or partially committed cells from the osteogenic or chondrogenic lineage, or combinations of any of the above.

In accordance with some embodiments, the material to be positioned in the hollow compartment of the mesh may be supplemented, further treated, or chemically modified with one or more bioactive agents or bioactive compounds. Bioactive agent or bioactive compound, as used herein, refers to a compound or entity that alters, inhibits, activates, or otherwise affects biological or chemical events. For example, bioactive agents may include, but are not limited to, osteogenic or chondrogenic proteins or peptides; DBM powder; collagen, insoluble collagen derivatives, etc., and soluble solids and/or liquids dissolved therein; anti-AIDS substances; anti-cancer substances; antimicrobials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamycin, etc.; immunosuppressants; anti-viral substances such as substances effective against hepatitis; enzyme inhibitors; hormones; neurotoxins; opioids; hypnotics; anti-histamines; lubricants; tranquilizers; anti-convulsants; muscle relaxants and anti-Parkinson substances; anti-spasmodics and muscle contractants including channel blockers; miotics and anti-cholinergics; anti-glaucoma compounds; anti-parasite and/or anti-protozoal compounds; modulators of cell-extracellular matrix interactions including cell growth inhibitors and antiadhesion molecules; vasodilating agents; inhibitors of DNA, RNA, or protein synthesis; anti-hypertensives; analgesics; anti-pyretics; steroidal and non-steroidal anti-inflammatory agents; anti-angiogenic factors; angiogenic factors and polymeric carriers containing such factors; anti-secretory factors; anti-coagulants and/or antithrombotic agents; local anesthetics; ophthalmics; prostaglandins; anti-depressants; anti-psychotic substances; anti-emetics; imaging agents; biocidal/biostatic sugars such as dextran, glucose, etc.; amino acids; peptides; vitamins; inorganic elements; co-factors for protein synthesis; endocrine tissue or tissue fragments; synthesizers; enzymes such as alkaline phosphatase, collagenase, peptidases, oxidases and the like; polymer cell scaffolds with parenchymal cells; collagen lattices; antigenic agents; cytoskeletal agents; cartilage fragments; living cells such as chondrocytes, bone marrow cells, mesenchymal stem cells; natural extracts; genetically engineered living cells or otherwise modified living cells; expanded or cultured cells; DNA delivered by plasmid, viral vectors, or other member; tissue transplants; autogenous tissues such as blood, serum, soft tissue, bone marrow, or the like; bioadhesives; bone morphogenetic proteins (BMPs including BMP-2); osteoinductive factor (IFO); fibronectin (FN); endothelial cell growth factor (ECGF); vascular endothelial growth factor (VEGF); cementum attachment extracts (CAE); ketanserin; human growth hormone (HGH); animal growth hormones; epidermal growth factor (EGF); interleukins, for example, interleukin-1 (IL-1), interleukin-2 (IL-2); human alpha thrombin; transforming growth factor (TGF-beta); insulin-like growth factors (IGF-1, IGF-2); parathyroid hormone (PTH); platelet derived growth factors (PDGF); fibroblast growth factors (FGF, BFGF, etc.); periodontal ligament chemotactic factor (PDLGF); enamel matrix proteins; growth and differentiation factors (GDF); hedgehog family of proteins; protein receptor molecules; small peptides derived from growth factors above; bone promoters; cytokines; somatotropin; bone digesters; antitumor agents; cellular attractants and attachment agents; immuno-suppressants; permeation enhancers, for example, fatty acid esters such as laureate, myristate and stearate monoesters of polyethylene glycol, enamine derivatives, alpha-keto aldehydes; and nucleic acids.

In certain embodiments, the bioactive agent may be a drug. In some embodiments, the bioactive agent may be a growth factor, cytokine, extracellular matrix molecule, or a fragment or derivative thereof, for example, a protein or peptide sequence such as RGD.

The material may have functional characteristics. Alternatively, other materials having functional characteristics may be incorporated into the mesh. Functional characteristics may include radiopacity, bacteriocidity, source for released materials, tackiness, etc. Such characteristics may be imparted substantially throughout the mesh or at only certain positions or portions of the mesh.

Suitable radiopaque materials include, for example, ceramics, mineralized bone, ceramics/calcium phosphates/calcium sulfates, metal particles, fibers, and iodinated polymer (see, for example, WO/2007/143698). Polymeric materials may be used to form the mesh and be made radiopaque by iodinating them, such as taught for example in U.S. Pat. No. 6,585,755, herein incorporated by reference in its entirety. Other techniques for incorporating a biocompatible metal or metal salt into a polymer to increase radiopacity of the polymer may also be used. Suitable bacteriocidal materials may include, for example, trace metallic elements. In some embodiments, trace metallic elements may also encourage bone growth.

In some embodiments, the mesh may comprise a material that becomes tacky upon wetting. Such material may be, for example, a protein or gelatin based material. Tissue adhesives, including mussel adhesive proteins and cryanocrylates, may be used to impart tackiness to the mesh. In further examples, alginate or chitosan material may be used to impart tackiness to the mesh. In further embodiments, an adhesive substance or material may be placed on a portion of the mesh or in a particular region of the mesh to anchor that portion or region of the mesh in place at a surgical site.

Bone Material

The bone material can be natural or synthetic bone material (e.g., tricalcium phosphate and/or hydroxyapatite). In various embodiments, the bone material may be particulated such as, for example, in bone chips, powder or fiber form. If the bone is demineralized, the bone may be made into a particulate before, during or after demineralization. In some embodiments, the bone may be monolithic and may not be a particulate.

The bone may be milled and ground or otherwise processed into particles of an appropriate size before or after demineralization. The particles may be particulate (for example, powder) or fibrous. The terms milling or grinding are not intended to be limited to production of particles of a specific type and may refer to production of particulate or fibrous particles. In certain embodiments, the particle size may be greater than 25 microns, such as ranging from about 25 to about 2000 microns, or from about 25 to about 500 microns or from about 200 to about 1000 microns. In some embodiments, the size of the bone particles are less than 100 microns. In some embodiments, the size of the bone particles are less than 500 microns.

After grinding, the bone particles may be sieved to select those particles of a desired size. In certain embodiments, the particles may be sieved though a 25 micron sieve, a 50 micron sieve, a 75 micron sieve, a 100 micron sieve, a 125 micron sieve, a 150 micron sieve, a 175 micron sieve and/or a 200 micron sieve.

In some embodiments, the bone material comprises DBM and/or mineralized bone. In some embodiments, the size of the bone material is less than 25 microns. In some embodiments, the bone material particle size is about 1, 2, 3, 4, 5, 6, 7, 8, 9, 10, 11, 12, 13, 14, 15, 16, 17, 18, 19, 20, 21, 22, 23, 24 and/or 25 microns.

In various embodiments, the bone powder, chips and/or the DBM and/or mineralized bone fibers have a sticky outer surface such that the bone material can adhere to DBM and/or mineralized bone fibers. In various embodiments, the bone powder is naturally sticky. In some embodiments, an adhesive agent is applied to the bone powder and/or the bone fibers comprising a bio-adhesive, glue, cement, cyanoacrylate, silicones, hot melt adhesives and/or cellulosic binders. In various embodiments, the adhesive may be applied to the surface of the bone powder by spraying or brushing. In some embodiments, a charge is applied to the fibers and an opposite charge is applied to the bone powder, (i.e., the technique of electrostatic precipitation). The bone powder will be attracted to, and tenaciously adhere to, the surface of the fiber. Any of these application techniques can be repeated one or more times to build up a relatively thick layer of adherent bone powder on the surface of the fibers.

The bone powder can be applied directly to the DBM fiber and/or fully mineralized fiber, chips and the mixture can be disposed in the mesh. In some embodiments, the bone material inserted into the mesh contains pores having a pore size from about 0.5 to about 2,000 microns. In some embodiments, bone material inserted into the mesh contains pores having a pore size of from about 0.5, 5, 50, 100, 150, 200, 250, 300, 350, 400, 450, 500, 550, 600, 650, 700, 750, 800, 850, 900, 950, 1,000, 1,050, 1,100, 1,150, 1,200, 1,250, 1,300, 1,350, 1,400, 1,450, 1,500, 1,550, 1,600, 1,650, 1,700, 1,750, 1,800, 1,850, 1,900, 1,950 to about 2,000 microns. In some embodiments, the pore size of the bone material is uniform. In some embodiments, the pore size of bone material is non-uniform and includes various pore sizes in the range from 0.5 to about 2,000 microns. Alternatively, the DBM fibers, chips, and DBM powder can be placed in a polymer (for example, collagen) and inserted into the bone implant.

Following shaving, milling or other technique whereby they are obtained, the bone material is subjected to demineralization in order to reduce its inorganic content to a very low level, in some embodiments, to not more than about 5% by weight of residual calcium and to not more than about 1% by weight of residual calcium. Demineralization of the bone material ordinarily results in its contraction to some extent.

Bone used in the methods described herein may be autograft, allograft, or xenograft. In various embodiments, the bone may be cortical bone, cancellous bone, or cortico-cancellous bone. While specific discussion is made herein to demineralized bone matrix, bone matrix treated in accordance with the teachings herein may be non-demineralized, demineralized, partially demineralized, or surface demineralized. This discussion applies to demineralized, partially demineralized, and surface demineralized bone matrix. In one embodiment, the demineralized bone is sourced from bovine or human bone. In another embodiment, demineralized bone is sourced from human bone. In one embodiment, the demineralized bone is sourced from the patient's own bone (autogenous bone). In another embodiment, the demineralized bone is sourced from a different animal (including a cadaver) of the same species (allograft bone).

In some embodiments, the bone material can be a combination of patient autograft bone and additional bone materials such as, for example, allograft, allograft DBM, ceramics and/or any of the bone material described above. In some embodiments, the combination bone material can have a ratio of 50:50 autograft bone to additional bone materials. In some embodiments, the combination bone material can have any ratio of autograft bone to additional bones materials, including, but not limited to, 25:75, 75:25, 10:90, 90:10, 20:80, 80:20, 30:70, 70:30, 40:60, or 60:40 autograft bone to additional bone materials.

In some embodiments, the bone material can be from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 to about 100% patient autograft bone, additional bone material or a combination thereof.

Any suitable manner of demineralizing the bone may be used. Demineralization of the bone material can be conducted in accordance with known conventional procedures. For example, in a preferred demineralization procedure, the bone materials useful for the implantable composition of this application are subjected to an acid demineralization step that is followed by a defatting/disinfecting step. The bone material is immersed in acid over time to effect its demineralization. Acids which can be employed in this step include inorganic acids such as hydrochloric acid and organic acids such as peracetic acid, acetic acid, citric acid, or propionic acid. The depth of demineralization into the bone surface can be controlled by adjusting the treatment time, temperature of the demineralizing solution, concentration of the demineralizing solution, agitation intensity during treatment, and other applied forces such as vacuum, centrifuge, pressure, and other factors such as known to those skilled in the art. Thus, in various embodiments, the bone material may be fully demineralized, partially demineralized, or surface demineralized.

After acid treatment, the bone is rinsed with sterile water for injection, buffered with a buffering agent to a final predetermined pH and then finally rinsed with water for injection to remove residual amounts of acid and buffering agent or washed with water to remove residual acid and thereby raise the pH. Following demineralization, the bone material is immersed in solution to effect its defatting. A defatting/disinfectant solution is an aqueous solution of ethanol, the ethanol being a good solvent for lipids and the water being a good hydrophilic carrier to enable the solution to penetrate more deeply into the bone. The aqueous ethanol solution also disinfects the bone by killing vegetative microorganisms and viruses. Ordinarily at least about 10 to 40 weight percent by weight of water (i.e., about 60 to 90 weight percent of defatting agent such as alcohol) should be present in the defatting/disinfecting solution to produce optimal lipid removal and disinfection within the shortest period of time. The concentration range of the defatting solution is from about 60 to 85 weight percent alcohol or about 70 weight percent alcohol.

Further in accordance with this application, the DBM material can be used immediately for preparation of the bone implant or it can be stored under aseptic conditions, advantageously in a critical point dried state prior to such preparation. In one embodiment, the bone material can retain some of its original mineral content such that the composition is rendered capable of being imaged utilizing radiographic techniques.

In various embodiments, this application also provides bone matrix compositions comprising critical point drying (CPD) fibers. DBM includes the collagen matrix of the bone together with acid insoluble proteins including bone morphogenic proteins (BMPs) and other growth factors. It can be formulated for use as granules, gels, sponge material or putty and can be freeze-dried for storage. Sterilization procedures used to protect from disease transmission may reduce the activity of beneficial growth factors in the DBM. DBM provides an initial osteoconductive matrix and exhibits a degree of osteoinductive potential, inducing the infiltration and differentiation of osteoprogenitor cells from the surrounding tissues.

DBM preparations have been used for many years in orthopedic medicine to promote the formation of bone. For example, DBM has found use in the repair of fractures, in the fusion of vertebrae, in joint replacement surgery, and in treating bone destruction due to underlying disease such as rheumatoid arthritis. DBM is thought to promote bone formation in vivo by osteoconductive and osteoinductive processes. The osteoinductive effect of implanted DBM compositions is thought to result from the presence of active growth factors present on the isolated collagen-based matrix. These factors include members of the TGF-β, IGF, and BMP protein families. Particular examples of osteoinductive factors include TGF-β, IGF-1, IGF-2, BMP-2, BMP-7, parathyroid hormone (PTH), and angiogenic factors. Other osteoinductive factors such as osteocalcin and osteopontin are also likely to be present in DBM preparations as well. There are also likely to be other unnamed or undiscovered osteoinductive factors present in DBM.

In various embodiments, the DBM provided in the kits, implants and methods described in this application is prepared from elongated bone fibers which have been subjected to critical point drying (CPD). The elongated CPD bone fibers employed in this application are generally characterized as having relatively high average length to average width ratios, also known as the aspect ratio. In various embodiments, the aspect ratio of the elongated bone fibers is at least from about 50:1 to at least about 1000:1. Such elongated bone fibers can be readily obtained by any one of several methods, for example, by milling or shaving the surface of an entire bone or relatively large section of bone.

In other embodiments, the length of the fibers can be at least about 3.5 cm and average width from about 20 mm to about 1 cm. In various embodiments, the average length of the elongated fibers can be from about 3.5 cm to about 6.0 cm and the average width from about 20 mm to about 1 cm. In other embodiments, the elongated fibers can have an average length from about 4.0 cm to about 6.0 cm and an average width from about 20 mm to about 1 cm.

In yet other embodiments, the diameter or average width of the elongated fibers is, for example, not more than about 1.00 cm, not more than 0.5 cm or not more than about 0.01 cm. In still other embodiments, the diameter or average width of the fibers can be from about 0.01 cm to about 0.4 cm or from about 0.02 cm to about 0.3 cm.

In another embodiment, the aspect ratio of the fibers can be from about 50:1 to about 950:1, from about 50:1 to about 750:1, from about 50:1 to about 500:1, from about 50:1 to about 250:1; or from about 50:1 to about 100:1. Fibers according to this disclosure can have an aspect ratio from about 50:1 to about 1000:1, from about 50:1 to about 950:1, from about 50:1 to about 750:1, from about 50:1 to about 600:1, from about 50:1 to about 350:1, from about 50:1 to about 200:1, from about 50:1 to about 100:1, or from about 50:1 to about 75:1.

In some embodiments, the chips to fibers ratio is about 90:10, 80:20, 75:25, 70:30, 60:40, 50:50, 40:60, 30:70, 25:75, 20:80 and/or 10:90. In various embodiments, a surface demineralized chips to fibers ratio is about 90:10, 80:20, 75:25, 70:30, 60:40, 50:50, 40:60, 30:70, 25:75, 20:80 and/or 10:90. In some embodiments, a surface demineralized chips to fully demineralized fibers ratio is about 90:10, 80:20, 75:25, 70:30, 60:40, 50:50, 40:60, 30:70, 25:75, 20:80 and/or 10:90.

In some embodiments, the DBM fibers have a thickness of about 0.5-4 mm. In various embodiments, the DBM fibers have a thickness of about 0.5, 0.6, 0.7, 0.8, 0.9, 1, 1.5, 2, 2.5, 3, 3.5 and/or 4 mm. In various embodiments, the ratio of DBM fibers to DBM powder is about 40:60 to about 90:10 W/W, W/V or V/V. In some embodiments, the ratio of mineralized bone fibers to DBM powder is about 25:75 to about 75:25 W/W, W/V or V/V. In various embodiments, the bone implant comprises DBM fibers and mineralized fibers in a ratio of 40:60 to about 90:10 W/W, W/V or V/V. In some embodiments, the DBM fibers to DBM powder ratio, mineralized bone fibers to DBM powder ratio and/or the DBM fibers and mineralized fibers ratio is from 5:95 to about 95:5 W/W, W/V or V/V. In some embodiments, the DBM fibers to DBM powder ratio, mineralized bone fibers to DBM powder ratio and/or the DBM fibers and mineralized fibers ratio is 5:95, 10:90, 15:85, 20:80, 25:75, 30:70, 35:65, 40:60, 45:55, 50:50, 55:45, 60:40, 65:35, 70:30, 75:25, 80:20, 85:15, 90:10 and/or 95:5 W/W, W/V or V/V.

In some embodiments, the bone material comprises demineralized bone material comprising demineralized bone, fibers, powder, chips, triangular prisms, spheres, cubes, cylinders, shards or other shapes having irregular or random geometries. These can include, for example, "substantially demineralized," "partially demineralized," or "fully demineralized" cortical and/or cancellous bone. These also include surface demineralization, where the surface of the bone construct is substantially demineralized, partially demineralized, or fully demineralized, yet the body of the bone construct is fully mineralized.

In various embodiments, the bone material comprises fully DBM fibers and surface demineralized bone chips. In some embodiments, the ratio of fully DBM fibers to surface demineralized bone chips is from 5:95 to about 95:5 fibers to chips. In some embodiments, the ratio of fully DBM fibers to surface demineralized bone chips is 5:95, 10:90, 15:85, 20:80, 25:75, 30:70, 35:65, 40:60, 45:55, 50:50, 55:45, 60:40, 65:35, 70:30, 75:25, 80:20, 85:15, 90:10 and/or 95:5 fibers to chips. In various embodiments, the fully DBM fibers have a thickness of about 0.5-4 mm. In various embodiments, the fully DBM fibers have a thickness of about 0.5, 0.6, 0.7, 0.8, 0.9, 1, 1.5, 2, 2.5, 3, 3.5 and/or 4 mm.

In various embodiments, the fibers and/or the powder is surface DBM. In some embodiments, the fibers and/or the powder is surface DBM cortical allograft. In various embodiments, surface demineralization involves surface demineralization to at least a certain depth. For example, the surface demineralization of the allograft can be from about 0.25 mm, 0.5 mm, 1 mm, 1.5 mm, 2.0 mm, 2.5 mm, 3.0 mm. 3.5 mm, 4 mm, 4.5 mm, to about 5 mm. The edges of the bone fibers and/or powder may further be machined into any shape or to include features such as grooves, protrusions, indentations, etc., to help improve fit and limit any movement or micromotion to help fusion and/or osteoinduction to occur.

To prepare the osteogenic DBM, a quantity of fibers is combined with a biocompatible carrier to provide a demineralized bone matrix.

DBM typically is dried, for example via lyophilization or solvent drying, to store and maintain the DBM in active condition for implantation. Moreover, each of these processes is thought to reduce the overall surface area structure of bone. As may be appreciated, the structural damage of the exterior surface reduces the overall surface area. Physical alterations to the surface and reduction in surface area can affect cell attachment, mobility, proliferation, and differentiation. The surface's affinity for growth factors and release kinetics of growth factors from the surface may also be altered.

Accordingly, in some embodiments, methods for drying bone to store and maintain the bone in active condition for implantation that maintains or increases the surface area of the bone are provided. In one embodiment, the bone matrix is treated using a critical point drying technique, thereby reducing destruction of the surface of the bone. While specific description is made to critical point drying, it is to be appreciated that, in alternative embodiments, super critical point treatment may be used. In various embodiments utilizing CPD, a percentage of collagen fibrils on the surface of the bone are non-denatured after drying to a residual moisture content of approximately 15% or less. In some embodiments, after drying, the bone matrix has a residual moisture content of approximately 8% or less. In some embodiments, after drying, the bone matrix has a residual moisture content of approximately 6% or less. In some embodiments, after drying, the bone matrix has a residual moisture content of approximately 3% or less.

Evaporative drying and freeze drying of specimens can cause deformation and collapse of surface structures, leading to a decrease in surface area. Without wishing to be bound by a particular theory, this deformation and structure is thought to occur because as a substance crosses the boundary from liquid to gas, the substance volatilizes such that the volume of the liquid decreases. As this happens, surface tension at the solid-liquid interface pulls against any structures to which the liquid is attached. Delicate surface structures tend to be broken apart by this surface tension. Such damage may be caused by the effects of surface tension on the liquid/gas interface. Critical point drying is a technique that avoids effects of surface tension on the liquid/gas interface by substantially preventing a liquid/gas interface from developing. Critical point or supercritical drying does not cross any phase boundary, instead passing through the supercritical region, where the distinction between gas and liquid ceases to apply. As a result, materials dehydrated using critical point drying are not exposed to damaging surface tension forces. When the critical point of the liquid is reached, it is possible to pass from liquid to gas without abrupt change in state. Critical point drying can be used with bone matrices to phase change from liquid to dry gas without the effects of surface tension. Accordingly, bone dehydrated using critical point drying can retain or increase at least some of the surface structure and therefore the surface area.

In some embodiments, critical point drying is carried out using carbon dioxide. However, other mediums such as Freon, including Freon 13 (chlorotrifluoromethane), may be used. Generally, fluids suitable for supercritical drying include carbon dioxide (critical point 304.25 K at 7.39 MPa or 31.1° C. at 1072 psi or 31.2° C. and 73.8 bar) and Freon (about 300 K at 3.5-4 MPa or 25 to 30° C. at 500-600 psi). Nitrous oxide has similar physical behavior to carbon dioxide, but is a powerful oxidizer in its supercritical state. Supercritical water is also a powerful oxidizer, partly because its critical point occurs at such a high temperature (374° C.) and pressure (3212 psi/647K and 22.064 MPa).

In some embodiments, the bone may be pretreated to remove water prior to critical point drying. Thus, in accordance with one embodiment, bone matrix is dried using carbon dioxide in (or above) its critical point status. After demineralization, bone matrix samples (in water) may be dehydrated to remove residual water content. Such dehydration may be, for example, through a series of graded ethanol solutions (for example, 20%, 50%, 70%, 80%, 90%, 95%, 100% ethanol in deionized water). In some embodiments, penetrating the tissue with a graded series of ethanol solutions or alcohols may be accomplished in an automated fashion. For example, pressure and vacuum could be used to accelerate penetration into the tissue.

Methods of Use

A method of implanting a bone implant at a surgical site beneath the skin of a patient is provided. The bone implant implanted by this method can be, for example, bone implant 10 shown in FIGS. 1-4 and 6A to 7B, and the implantation site corresponds to minimally invasive midline lumbar fusion, posterior cervical fusion and oral maxillofacial repair procedures. The implantation site can also correspond to healing vertebral compression fractures, interbody fusion, additional minimally invasive procedures, posterolateral fusion procedures, correction of adult or pediatric scoliosis, treating long bone defects, osteochondral defects, ridge augmentation (dental/craniomaxillofacial, e.g. edentulous patients), beneath trauma plates, tibial plateau defects, filling bone cysts, wound healing, around trauma, contouring (cosmetic/plastic/reconstructive surgery), and others.

The method can also be employed in a surgical treatment with a patient in a prone or supine position, and/or employ various surgical approaches to the spine, including anterior, posterior, posterior mid-line, direct lateral, and/or antero-lateral approaches, and in other body regions. The method may also be employed with procedures for treating the lumbar, cervical, thoracic, sacral and pelvic regions of a spinal column. The method may also be used on animals, bone models and other non-living substrates, such as, for example, in training, testing and demonstration.

The method of implanting a bone implant at a surgical site comprises, providing a bone implant 10 comprising a mesh 14 having an inner surface 16 and an outer surface 18 opposing the inner surface, the inner surface configured to receive a bone material 12 when the inner surface of the mesh is in an open configuration; a plurality of projections 24 disposed on or in at least a portion of the inner surface of the mesh, the plurality of projections extending from at least the portion of the inner surface of the mesh and configured to engage a section of the inner surface of the mesh or a section of the outer surface of the mesh or both sections of the inner and outer surfaces of the mesh in a closed configuration so as to enclose the bone material; disposing the bone material into the inner surface of the mesh; enclosing the bone material in the mesh; and placing the bone implant at the surgical site thereby implanting the bone implant at the surgical site.

The plurality of projections are the hooks described herein, and the section of the inner surface may also comprise the plurality of recesses, such as loops, as described herein, that are configured to mate with the plurality of projections of the inner surface. The bone material can be fully demineralized bone fibers and surface demineralized bone chips.

Figure 5B:
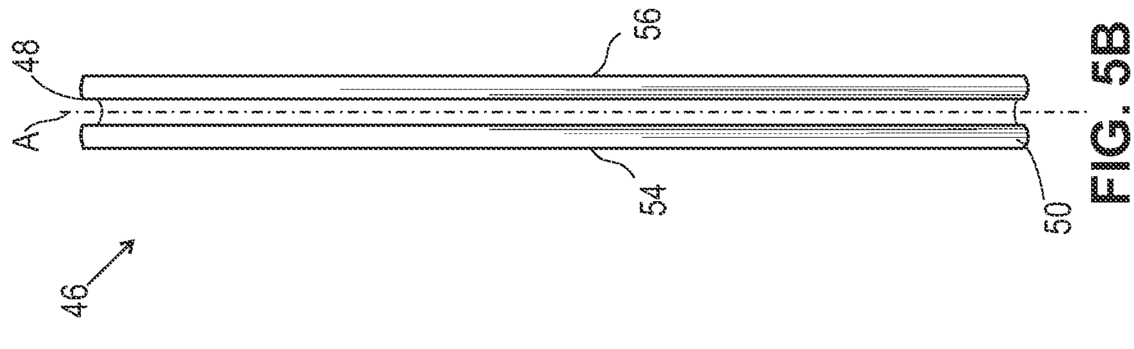
FIG. 5B illustrates a top view of the tray of FIG. 5A in a closed configuration with the ends open.
Figure 5A:
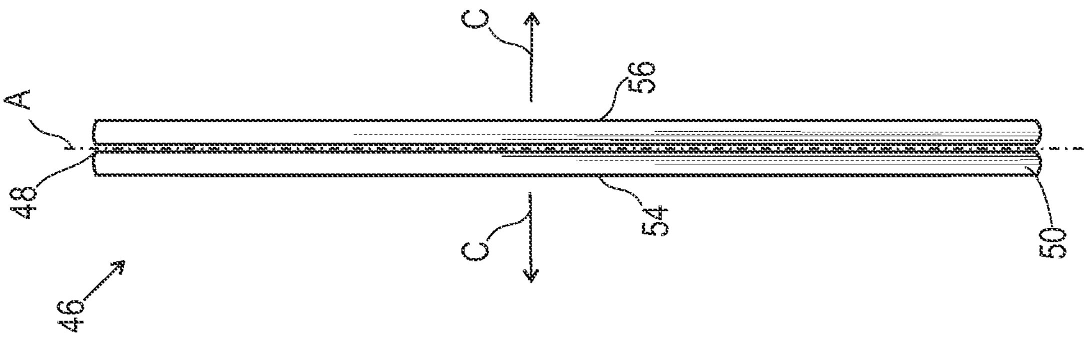
FIG. 5A illustrates a top view of a tray in a closed configuration. The tray has a proximal end, a distal end, and a longitudinal recess disposed therebetween. The longitudinal recess is configured to receive a bone implant comprising a mesh in an open configuration to allow filling of bone material into the bone implant.

A method of making bone implant 10 is provided, the method comprising, placing the mesh 14 onto tray 46; disposing bone material 12 onto the inner surface of the mesh material in a fill zone area that corresponds to an area above the longitudinal recess of the tray; folding a section of the inner surface of the mesh such that the mesh defines a compartment; sealing the compartment by moving the first and second tray sections in an upward direction, as shown by arrows B in FIG. 6C such that the tray is in a closed configuration; removing the bone implant from the tray by moving the first and second tray sections in a downward direction, as shown by arrows C in FIG. 5A; and cutting the mesh material into a selected size and shape for implantation at a selected surgical site. In some embodiments, the tray can be in an open configuration and designed to hold the mesh so that it can be filled with bone material. Thus, the tray can be stationary and the user merely grasps the mesh after it is filled with the bone material and seals the edges of the mesh via the projections.

In some embodiments, the bone implant can be sealed manually by a user, as shown by FIG. 7A, by the user applying pressure to the outer surface of the mesh such that the plurality of projections engage a portion of the inner surface and/or section comprising a plurality of projections and/or recesses. The mesh can alternatively be rolled by the user to seal the bone implant, as shown in FIG. 7B.

In some embodiments, the bone implant may be used in healing vertebral compression fractures, interbody fusion, minimally invasive procedures, posterolateral fusion, correction of adult or pediatric scoliosis, treating long bone defects, osteochondral defects, ridge augmentation (dental/craniomaxillofacial, e.g. edentulous patients), beneath trauma plates, tibial plateau defects, filling bone cysts, wound healing, around trauma, contouring (cosmetic/plastic/reconstructive surgery), and others. The bone implant may be used in a minimally invasive procedure via placement through a small incision, or other means. The size and shape may be designed with restrictions on delivery conditions.

In some embodiments, the bone implant is flexible enough so that it can be folded upon itself before it is implanted at, near, or in the surgical site.

Generally, the bone implant may be applied to a preexisting defect, to a created channel, or to a modified defect. Thus, for example, a channel may be formed in a bone, or a pre-existing defect may be cut to form a channel, for receipt of the bone implant. The bone implant may be configured to match the channel or defect. In some embodiments, the configuration of bone implant may be chosen to match the channel. In other embodiments, the channel may be created, or the defect expanded or altered, to reflect a configuration of the bone implant. The bone implant may be placed in the defect or channel and, optionally, coupled using attachment mechanisms.

Although the invention has been described with reference to embodiments, persons skilled in the art will recognize that changes may be made in form and detail without departing from the spirit and scope of the invention

What is claimed is:

1. A kit for filling bone material in a bone implant, the kit comprising:
- a bone implant comprising a mesh having an inner surface and an outer surface opposing the inner surface, the inner surface configured to receive a bone material when the inner surface of the mesh is in an open configuration, and the inner surface has a center and a perimeter along a longitudinal axis;
- a mating section disposed on the center of the inner surface of the mesh, the mating section having a longitudinal recess extending along the longitudinal axis and configured to receive the bone material when the mesh is in the open configuration;
- a plurality of projections disposed on or in at least a portion of the inner surface of the mesh, the plurality of projections extending from at least the portion of the inner surface of the mesh and configured to engage the mating section of the inner surface in a closed configuration so as to enclose at least a portion of the bone material within the mating section; and
- a tray having a proximal end, a distal end, and a longitudinal recess disposed therebetween, the longitudinal recess configured to receive and support the mating section of the mesh in the open configuration to allow filling of the bone material into the bone implant.

2. A kit of claim 1, wherein the recess of the tray forms a slot for receiving the mesh.

3. A kit of claim 1, wherein the longitudinal recess is a channel, a trough, a slot, a groove or grooves, an indent or indents or a combination thereof.

4. A kit of claim 1, wherein the longitudinal recess is centrally located in the tray.

5. A kit of claim 1, wherein the tray is made of a metal, thermoform, a polymer or a combination thereof.

6. A kit of claim 1, wherein (i) the bone material comprises fully demineralized bone fibers and surface demineralized bone chips; (ii) the bone material comprises calcium phosphate; or (iii) the bone material comprises autograft.

7. A method of implanting a bone implant at a surgical site, the method comprising:
- providing a bone implant comprising a mesh having an inner surface and an outer surface opposing the inner surface, the inner surface configured to receive a bone material when the inner surface of the mesh is in an open configuration, the inner surface having a mating section disposed on a center of the inner surface, the mating section having a longitudinal recess;
- a plurality of projections disposed on or in at least a portion of the inner surface of the mesh, the plurality of projections extending from at least the portion of the inner surface of the mesh and configured to engage the mating section of the inner surface in a closed configuration so as to enclose the bone material;
- supporting the mating section of the mesh within a longitudinal recess of a tray while the mesh is in the open configuration;
- disposing the bone material into the longitudinal recess of the mating section by orientating the mesh in the open configuration;

enclosing the bone material in the mesh by orientating the mesh in the closed configuration such that at least a portion of the bone material is enclosed within the mating section; and
- placing the bone implant at the surgical site thereby implanting the bone implant at the surgical site.

8. A method according to claim 7, wherein (i) the plurality of projections are hooks; (ii) the inner surface comprises a plurality of recesses configured to mate with the plurality of projections of the inner surface; or (iii) the bone material is fully demineralized bone fibers and surface demineralized bone chips.

9. A kit of claim 1, wherein (i) the mesh is foldable in the closed configuration to enclose the bone material; (ii) the inner surface of the mesh comprises a fold line extending from a distal end to a proximal end of the inner surface, the fold line forming a compartment to receive the bone material; (iii) the mesh is configured to roll the section of the inner surface over the bone material to enclose the bone material; (iv) the plurality of projections are disposed on or in the entire inner surface of the mesh or (v) the section of the inner surface comprises a plurality of recesses configured to mate with the plurality of projections of the inner surface.

10. A kit of claim 1, wherein the bone material is partially enclosed by the mesh.

11. A kit of claim 1, wherein the inner surface of the mesh comprises a distal end and a proximal end and a compartment extending from the distal end to the proximal end, the compartment configured to receive the bone material, the compartment having none of the plurality of the projections.

* * * * *